(12) United States Patent
Kohn et al.

(10) Patent No.: US 8,535,921 B2
(45) Date of Patent: *Sep. 17, 2013

(54) PROCESS TO PRODUCE ORGANIC COMPOUNDS FROM SYNTHESIS GASES

(76) Inventors: Richard Allen Kohn, Columbia, MD (US); Seon-Woo Kim, Elkridge, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/430,203

(22) Filed: Mar. 26, 2012

(65) Prior Publication Data

US 2012/0270288 A1    Oct. 25, 2012

Related U.S. Application Data

(63) Continuation of application No. 13/260,587, filed on Sep. 27, 2011, now Pat. No. 8,178,329, and a continuation of application No. PCT/US2010/029707, filed on Apr. 1, 2010.

(60) Provisional application No. 61/165,654, filed on Apr. 1, 2009.

(51) Int. Cl.
  *C12P 7/16*       (2006.01)
  *C12N 1/00*       (2006.01)

(52) U.S. Cl.
  USPC .......................................... 435/160; 435/243

(58) Field of Classification Search
  USPC ................................. 435/160, 243
  See application file for complete search history.

(56) References Cited

U.S. PATENT DOCUMENTS

| | | | |
|---|---|---|---|
| 5,173,429 | A | 12/1992 | Gaddy |
| 5,593,886 | A | 1/1997 | Gaddy |
| 6,136,577 | A | 10/2000 | Gaddy |
| 7,285,402 | B2 | 10/2007 | Gaddy |
| 2008/0176301 | A1 | 7/2008 | Granda |

OTHER PUBLICATIONS

Shen et al. ,Appl. Microbiol. Biotechnol. 51, 827-832 (1999).*
Grethlein et al., J. Ferment. Bioeng. 72, 58-60 (1991).*
Lovitt, R. W., R Longin, and J. G. Zeikus. Ethanol prouction by thermphilic bacteria: physiological comparison of solvent effects on parent and alcohol-tolerant strains fo *Clostridium thermohydrosulfuricum*. Applied Environmental Microbiology, Jul. 1984. vol. 48 (1) pp. 171-177.
Henstra, A. M., J. Sipma, A. Rinzema, A. J. M. Stams. "Microbiology of synthesis gas fermentation for biofuel production." Current Opinion in Biotechnology, Jun. 2007, vol. 18 (3) pp. 200-206.
Younesi, H., G. Najafpour, A. R. Mohamed. "Ethanol and acetate production from synthesis gas via fermentation processes using anaerobic bacterium, *Clostridium ljungdahili*" Biochemical Engineering Journal, Dec. 2005, vol. 27 (2) pp. 110-119.
Klasson, K. T., M. D. Ackerson, E. C. Clausen, J. L. Gaddy. "Bioconversion of synthesis gas into liquid or gaseous fuels" Enzyme and Microbial Technology, Aug. 1992: vol. 14: (8) 602-808.
Fischer, C. R., D.Klein-Marcuschamer, G. Stephanopoulos. "Selection and optimization of microbial hosts for biofuels production" Metabolic Engineering, Nov. 2008, vol. 10 (6) pp. 295-304.
Atsumi, S., A.F. Cann, M. R. Connor, C. R. Shen, K. M Smith, M. P. Brynildsen. "Metabolic engineering of *Escherichia coli* for 1-butanol production" Metabolic Engineering, Nov. 2008. vol. 10(6) 305-311.
Atsumi, S., T. Hanai, and J. C. Liao. "Non-fermentative pathways for synthesis of branched-chain higher alcohols as biofuels". Nature. (Jan. 2008) vol. 451:pp. 86-89.
Pind,P. "Dynamics of the anaerobic process: effects of volatile fatty acids", Biotechnology and Bioengineering. (Jun. 30, 2003). vol. 82: (7) pp. 791-801.
Ezeji, T. C., N. Qureshi, Blaschek, H. P. "Bioproduction of butanol from biomass: from genes to bioreactors". Current Opinion in Biotechnology (Apr. 2007) vol. 16 pp. 220-227.

\* cited by examiner

*Primary Examiner* — Chih-Min Kam

(57) ABSTRACT

At least one isolated microorganism and a fermentation method to convert hydrogen gas, carbon dioxide gas, and/or carbon monoxide gas to a lower alkyl alcohol and/or carboxylic acid and to produce at least 2% by volume of the lower alkyl alcohol or carboxylic acid in an aqueous-based medium.

20 Claims, 10 Drawing Sheets

PROCESS TO PRODUCE ORGANIC COMPOUNDS FROM SYNTHESIS GASES

RELATED APPLICATIONS

This application is a continuation of U.S. patent application Ser. No. 13/260,587, filed Sep. 27, 2011 now U.S. Pat. 8,178,329, and it claims priority to PCT Application No. PCT/US2010/029707, filed Apr. 1, 2010, which claims priority to U.S. Provisional Patent Application No. 61/165,654, filed Apr. 1, 2009.

BACKGROUND OF THE INVENTION

1. Field of the Invention

The present invention relates to a process for producing organic compounds such as lower alkyl alcohols, including ethanol, propanol (e.g. 1-propanol, iso-propanol), and butanol (e.g. 1-butanol), from gases including carbon dioxide, carbon monoxide, and hydrogen under thermodynamically favorable conditions; microorganisms used in the process to produce organic compounds from gases; and a process for enriching, isolating, and improving microorganisms that can be used in the process to produce organic compounds from gases. The process may also be used to produce one or more carboxylic acids including acetic acid, propionic acid, or butyric acid, other carboxylic acids, especially longer carboxylic acids, and the process produces animal feeds, and can be used to produce other products.

2. Description of the Background

Currently most fuel ethanol produced in the U.S. is made from corn grain. Even if all the corn grain produced in the US were converted to ethanol, it would only supply about 15% of our current transportation fuel needs. Thus, there is a pressing need to produce fuel ethanol and other alcohols from other sources of feedstock. If ethanol could be inexpensively produced from plant fiber, waste biomass like leaves, paper, manure, wood byproducts, and others materials, it could offset fuel shortages. Plant fiber, also called cellulosic biomass, can be grown on marginal land and in greater yields than grain crops. Eventually, the U.S. aims to use up to a billion tons of such biomass per year. Other waste biomass includes garbage comprised of waste plastic or other forms of fossil fuel derivatives.

Plant fiber is also called plant cell wall, which is comprised of cellulose, hemicellulose, pectin, and lignin. There are a few processes available for the production of ethanol from plant fiber. One process is physical conversion: biomass is heated to high temperatures, such as 650° F. The biomass is degraded to carbon monoxide (CO) and hydrogen ($H_2$), and subsequently these gases are converted to ethanol by a catalytic or microbial process. The advantage of this approach is that many forms of biomass or fossil fuel derivatives can be used, but the cost of facilities may be high compared to anaerobic digestion. In addition, waste gases from other industrial processes can be used, or even gases produced by anaerobic digestion can be efficiently used.

Use of microorganisms to produce acetic acid or ethanol from $CO_2$, CO and $H_2$ was disclosed in U.S. Pat. Nos. 5,173,429; 5,593,886; and 6,136,577, which are incorporated herein by reference. However, the ratio of acetic acid to ethanol was 20:1 or greater and only 0.1% ethanol concentration could be achieved. In U.S. Pat. No. 7,285,402, incorporated herein by reference, ethanol concentrations greater than 10 g/L and acetate concentrations lower than about 8-10 g/L were claimed, while continuing to permit culture growth and good culture stability. However, the cost of achieving these rates through physical manipulations of the fermentation, and the cost of distillation for such low concentrations of ethanol would be cost prohibitive for an industrial process.

A second approach is called biochemical conversion: the biomass is boiled in caustic acids or other chemicals to hydrolyze the cellulose and hemicellulose. The residue is neutralized and conditioned and subjected to cellulolytic enzymes to release sugars. The glucose released is fermented by yeast to ethanol, and the 5-carbon sugars are separated and converted to ethanol by a separate organism.

A third approach to producing cellulosic ethanol would be to use living microorganisms that can digest cellulose, hemicellulose and pectins and convert them to ethanol. This approach would be least expensive because it does not require harsh chemicals or high temperatures and uses fewer processing steps. However, the approach is only feasible if there is a microorganism, or mixed culture of microorganisms, that can readily digest cellulose and hemicellulose, and which, preferably converts a significant part of the carbohydrate to ethanol. The ideal organisms would also be tolerant to ethanol concentrations so that they can be used to digest considerable carbohydrate to ethanol at high enough concentration to decrease the cost of distillation.

Microorganisms can be used for aspects of all three processes. In the first case, microorganisms can assimilate the synthesis gases, such as $CO_2$, CO and $H_2$ into ethanol or acetic acid, or into longer chain alkyl alcohols (e.g. 1-propanol, 1-butanol) or longer chain carboxylic acids (e.g. propionate, butyrate). In the second case, organisms are used to produce enzymes for the degradation of plant fiber and for fermentation of sugars into ethanol. In the third case, microorganisms are used to both digest plant biomass and convert it to alcohols. Finally, microbial cultures that can both digest biomass (case 3) and assimilate gases into alcohols (case 1) can be used. In this case, the gases that are produced by organisms in the digestion of the biomass can be converted to ethanol or other alcohols.

For either the first or the third process, or a combination thereof, two desired characteristics of the microorganisms used are: 1) ability to convert a large portion of the substrate (e.g. gases or biomass) to the desired products (e.g. alcohols or acids), and 2) ability to continue producing the desired product even in the presence of high concentrations of those products. Currently, microorganisms are not available for conversion of synthesis gases to high concentrations of alkyl alcohols. The ability to tolerate high concentrations of products, and to still produce more of the product at high concentrations (about 5% to about 6%, by volume), would make it possible to produce the products in a way in which it is cost effective to separate and utilize the products.

SUMMARY

The disclosed invention is for a process to produce products of fermentation wherein the fermentation is controlled by establishing conditions that make it thermodynamically favorable to produce desired products over other products that might otherwise be produced. Further, the invention comprises microbial cultures that produce specific desired products for use in the process, and the invention comprises a process to enrich and isolate microorganisms that produce desired products of the fermentation.

One use of the process is to convert synthesis gases (e.g. $CO_2$, CO and $H_2$) to lower alkyl alcohol or desired organic acids under conditions that make it thermodynamically feasible or thermodynamically favorable to produce the desired products.

Another aspect of this invention comprises selected microbial cultures that can produce efficiently lower alkyl alcohols including ethanol, propanol or butanol from synthesis gases. The volumes of ethanol in cultures reached at least, 1%, more preferably at least about 2%, 3%, 4%, 5%, 6%, 7%, 8%, 9%, 10%, 11% or 12%.

The volumes of butanol in culture were at least 0.5%, preferably at least about 1%, 2%, 3%, 4%, 5%, 6% or 7%.

The volumes of propanol in culture were at least 0.5%, preferably at least about 1%, 2%, 3%, 4%, 5%, 6% or 7%.

These microbial cultures convert a large portion of the gas mass to the desired alkyl alcohol. For example, in one embodiment, up to at least about 95% of VFA plus lower alcohol content was ethanol plus butanol, especially 1-butanol.

The microbial cultures are also tolerant to the alkyl alcohol, and continue to grow in the presence of high concentrations of alkyl alcohol, and continue to produce alkyl alcohol in the presence of high concentrations of alkyl alcohol.

A further aspect of the application comprises microbial cultures that can both degrade biomass such as cellulosic biomass to alkyl alcohol, and can assimilate produced and perfused gases to produce additional alkyl alcohol.

In addition, another aspect of the application invention comprises a process for producing cultures of microorganisms that convert a high percentage of the biomass to a desired alkyl alcohol, and can tolerate high concentrations of the desired alkyl alcohols.

Another aspect of the application comprises producing products from synthesis gases ($CO_2$, CO and $H_2$) using undefined mixed cultures, in which a mixture of products can be produced.

In addition to alcohols, co-products that can be produced with the process include: carboxylic acids such as volatile fatty acids ("VFA"), which can be converted to other products or used for various purposes, and microbial protein, which can be used as an animal feed.

This application also comprises a method for production of specific VFA or longer carboxylic acids, which can be separated and used for other industrial processes or converted to other products.

DETAILED DESCRIPTION OF THE PREFERRED EMBODIMENTS

Term Definitions

Figure 1:
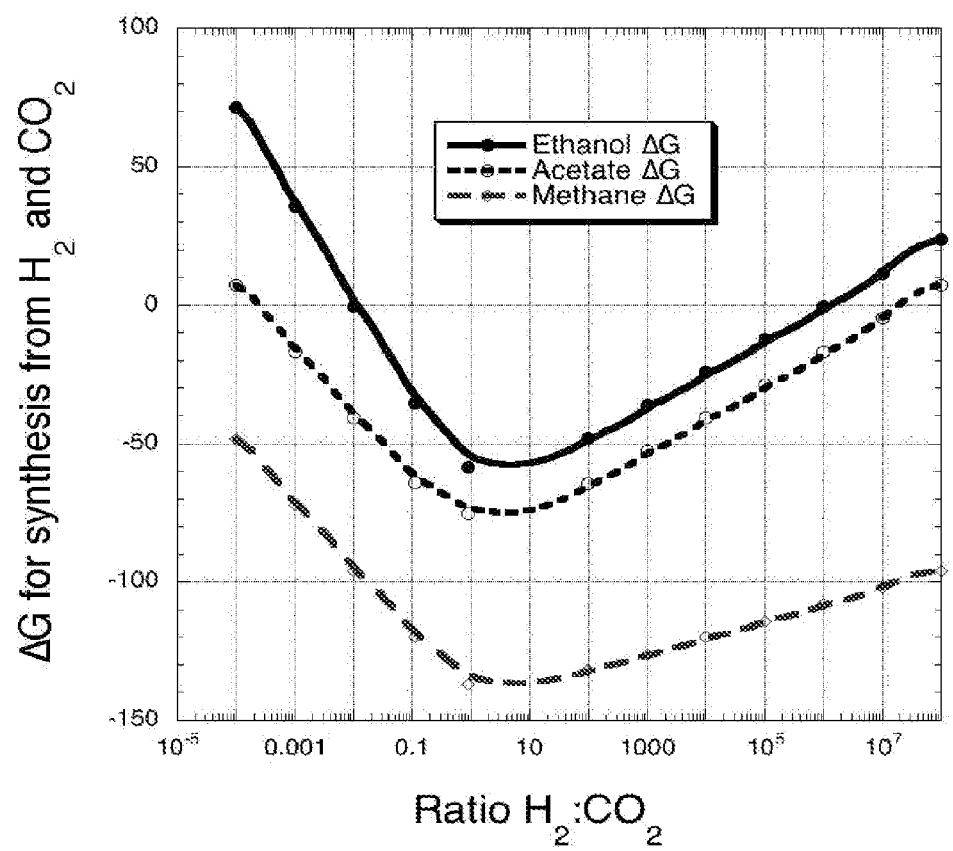
FIG. 1 indicates the change in free energy ($\Delta G$, kJ/mol) for synthesis of ethanol, acetate or methane from $H_2$ and $CO_2$ as the molar ratio of $H_2$ to $CO_2$ increases. This figure shows the energy available for forming different products peaks at a ratio of about 2 to 4. The model assumes the process takes place at 1 atmospheric total pressure, 0.1 atmospheres methane, and 0.001 M each aqueous acetate and ethanol, at 39° C., pH 6.5.

Aerotolerant: means the microorganism is able to grow in the presence of open air, such as an open flask because oxygen is not toxic to the organism.

Alcohol tolerant: means that the microorganism is able to grow in the presence of alcohols. Generally this means an amount of total alcohols (e.g. ethanol+propanol+butanol) of at least about 0.5% to about 1% by volume, and preferably about 2% by volume, in an aqueous medium.

Butanol tolerant: means that the microorganism is able to grow in the presence of butanol. Generally, this means an amount of butanol of at least 0.5% to 1% by volume, and preferably about 2% by volume of aqueous medium.

Carboxylic acid: means an organic compound containing the carboxyl group COOH or COO⁻ making it an organic acid because the proton (H⁺) can be donated. Carboxylic acids range in length from 1 to many carbons, such as greater than 20 carbons. Carboxylic acids are also called organic acids. The short-chain carboxylic acids ($C_2$ to $C_5$) are also called volatile fatty acids (VFA). Carboxylic acids are readily inter-converted with their conjugate base (acid having released a proton to solution) in aqueous solutions and thus production of the acid or the base form is considered production of either form as they can be readily inter-converted by adjusting pH of the solution.

Conjugate base: is one of two members of a pair of compounds that can be interconverted by gain or loss of a proton (H⁺). The conjugate base accepts a proton from solution wherein the conjugate acid donates a proton. For example, for acetic acid the acid form is referred to as the conjugate acid and acetate is referred to as the conjugate base. Near neutral pH (e.g. about 5 to about 7), most acid-base pairs of volatile fatty acids are predominantly in the conjugate base form. Furthermore, when free energy is calculated based on acid and base concentrations, the concentration of conjugate base was used with the associated concentration of protons (H⁺). A process that produces an acid or its conjugate base and a proton are considered equivalent because the two forms are readily interconverted.

Defined cultures: Cultures of microorganisms that have been isolated and at least partially characterized e.g. possibly identified as genus and species, or phylogenetically characterized by sequencing the variable region of 16S rRNA, or by sequencing the complete genome.

Direct evolution: means to direct the development of microorganisms that are well suited, preferably particularly well suited, for a given environment that is different from the environment from which the organism was taken, thereby changing the organism to be better suited to the new environment.

Directed equilibrium: means a process in accordance to the invention in which a system is allowed to move toward equilibrium, but concentrations of reactants and products within the system are manipulated, and possibly some reactions are directly inhibited, to direct the system to produce different products than would otherwise be produced as equilibrium is approached.

Ethanol tolerant: means that a microorganism is able to grow in the presence of ethanol. Generally, this means an amount of ethanol of at least about 0.5% to about 1% ethanol by volume, and preferably about 2% by volume of aqueous medium.

Favor: means the concentrations of reactants and products for competing reactions in the system, such as fermentation, are such that a greater decrease in free energy (more negative $\Delta G$) results from one reaction compared to another, where the first reaction is said to be favored over the other or others. For example, synthesis of acetate may be said to be favored over synthesis of ethanol under certain conditions, or alternatively acetate synthesis may be said to be favored over acetate degradation under certain conditions.

Favorable Free Energy for Synthesis: means the change in Gibbs Free Energy ($\Delta G$) is negative for the combination of reactions that comprise the system that converts a set of reactants to a set of products, and the system can therefore convert the reactants to products. The $\Delta G$ is calculated based on the change in Gibbs Free Energy under standard conditions ($\Delta G°$) of temperature and the concentrations or partial pressures of reactants and products. The $\Delta G°$ is calculated as the difference in Gibbs Free Energy of Formation ($\Delta G°_f$) for the products and reactants. The $\Delta G°_f$ is the $\Delta G$ for formation of any material from the elements i.e. graphite, $H_2$, $O_2$, for example, under standard conditions. Standard conditions means standard temperature (298.15 K unless otherwise indicated), 1 molar concentration of all solutes of reactants and products and 1 atmosphere partial pressure of gases combined.

Fermentation or fermentation system: refers to the use of microorganisms to produce a product by, for example, the conversion of infused gases to acetate or ethanol; where the fermentation or the fermentation system refers to the totality of all possible reactions which occur during digestion.

Isolated microorganisms: means one or more microorganisms that either have been isolated from a natural environment and grown in culture, or that have been developed using the methodologies from the present invention and grown in culture. Some are highly pure, originally from single, picked colonies. However, in the context, 'isolate' can refer to a culture enriched for a bacterium or bacteria with desired properties, where the desired bacteria is at least 5% of the culture, preferably 10%, 20%, 30%, 40%, 50%, 60%, 70%, 80%, 90% or 100%.

Lower alkyl alcohols: means $C_2$ to $C_5$ alcohols, i.e. ethanol, propanol and butanol.

Mixed cultures: More than one isolate of microorganism cultured together, may be defined or undefined, pure or impure cultures.

Molar proportion: means the molar concentration of one product as a proportion of the molar concentration of all of a type of product. For example, the molar proportion of butyrate of 50% of all volatile fatty acids means that the number of moles per liter of butyrate is 50% of the total moles per liter of all volatile fatty acids.

Molar ratio: Means the molar concentration of one product over the molar concentration of another product. For example, a molar ratio of 1 for ethanol to acetate means the concentration of ethanol in moles per liter is equal to the concentration of acetate in moles per liter. The molar ratio of gases can also be determined based on the moles of gas per unit volume and pressure of the total gas.

Partial pressure of a gas: means the pressure a given species of gas. For example, if the total gas pressure is 1 atmosphere (atm) and carbon dioxide comprises 20% of the total gas by volume, the partial pressure of carbon dioxide would be 0.2 atm or 20% of the total gas pressure.

Plant fiber: Defined chemically as comprising cellulose, hemicellulose, pectin or lignin, or combination thereof, and found in plant cell wall and many forms of feedstock including whole plants, biofuel crops (e.g. switchgrass, algae), food byproducts, wood, wood byproducts, paper, waste, animal manure, human manure, and others.

Propanol tolerant: means that a microorganism is able to grow in the presence of propanol. Generally, this means an amount of propanol of at least 0.5 to 1% propanol by volume, and preferably about 2% propanol by volume in aqueous media.

Pure cultures: Cultures of microorganisms that have been isolated or partially isolated to eliminate contaminant microorganisms. Cultures can be a single isolate or multiple isolates (mixed cultures).

Rumen microorganisms: means any or all of the microorganisms found in the rumen of ruminant animals. This includes a diverse array of archaea, bacteria, protozoa, and fungi that digests fibrous plant material and ferments starches and sugars, for example. Many of these organisms also use metabolites transferred from other organisms such as sugars released by digestion, VFA exported from other organisms, or $H_2$ and $CO_2$. This term also includes such microorganisms that are also found elsewhere in addition to the rumen including the digestive tract of animals, feces, silages, sludge, or in soil among other places.

Synthesis gases: means gases used to synthesize products. In the present invention the synthesis gases are usually carbon dioxide ($CO_2$), carbon monoxide (CO), and hydrogen gas ($H_2$).

Thermodynamically favorable: means the concentrations of reactants and products are such that the reaction is favored over other reactions.

Thermodynamically feasible: means the process can proceed spontaneously in the forward direction according to the second law of thermodynamics. In a thermodynamically feasible reaction, the multiplicative product of reaction product concentrations divided by the multiplicative product of reactant concentrations is low enough for the reaction to proceed spontaneously in the forward direction according to the calculation of the $\Delta G$ for the reaction. Observation of a reaction proceeding in the forward direction indicates that the reaction is feasible in consideration of all linked processes that enable the reaction to occur.

Total gas pressure: means the gas pressure in the fermentation system including all gases whether added to the process or produced in the fermentation.

Undefined cultures: means cultures of microorganisms taken from a source without having isolated individual microbes or characterized individual organisms.

VFA: means volatile fatty acids (e.g. acetic acid, propionic acid, butyric acid, iso-butyric acid, valeric acid, isovaleric acid, succinic acid, and lactic acid).

Basis of the Invention

This application is based in part on the use of the second law of thermodynamics to control fermentation and on the discovery of microorganisms that can convert $CO_2$, CO and $H_2$ to a much higher concentration of ethanol or other alcohols than previously known. For example, the concentration of ethanol can exceed about 10% by volume or the concentration of 1-butanol or 1-propanol can exceed about 6% by volume. In addition, nearly all the synthesis gases can be converted directly to alcohol with little production of acetic acid or other byproducts.

Models of fermentation developed by the inventor form the basis of the process. These models incorporate the laws of thermodynamics and kinetics to explain and predict the profile of products from fermentation. The models make it possible to establish conditions in a fermentation to favor desired products and to select and improve microorganisms that make those products.

All chemical reactions are controlled kinetically or thermodynamically. With kinetic control, the rates of reactions depend on substrate concentrations or enzyme activities, and these enzyme activities in turn depend on microbial growth or enzyme synthesis. The profile of products formed depends on the relative rates of the different competing reactions. With thermodynamic control, the rates of reactions and which pathway branches and direction are available depend on the concentrations of reactants and products.

Biologists have focused on controlling kinetic elements of fermentation such as enzyme function, microbial activity, gene expression, or provision of substrates. However, the inventors discovered that fermentation is often controlled by thermodynamics. For example, in a mixed-culture anaerobic digester, as soon as a glucose molecule is released by digestion of cellulose there are several microorganisms that can transport it into their cells and metabolize it to any number of products. The amount of energy any particular organism can obtain depends on the concentration of all the products of the reaction relative to all the reactants. Since the free glucose concentration is very low due to competition among microorganisms in the fermentation, and the products of fermentation are removed slowly, only very efficient microbes can use the small amount of glucose at all. And they can only use it when concentrations of the products they produce are low. Therefore, when their products start to build up, they can no longer obtain energy by converting the reactant to a product, and they leave the glucose behind for another microbe that produces a different product. In this way, a constant ratio of products is produced.

In chemistry, whether or not a reaction can proceed spontaneously in the forward direction is represented by the change in free energy ($\Delta G$), which can be calculated based on the ratio of products and reactants in the system. Using this calculation, a strongly negative $\Delta G$ indicates that the reaction could proceed strongly in the forward direction without the addition of energy to the system. A strongly positive value of $\Delta G$ indicates the reaction can not proceed in the forward direction without addition of energy to the system, and it may even run in the reverse direction.

If one calculates the $\Delta G$ values between many of the products in the rumen of a cow assuming typical metabolite concentrations, one finds that they are usually very near to 0. Additional products cannot be made unless the reactant concentrations increase or the product concentrations decrease. If one product increases, $\Delta G$ for that reaction increases, thus different products of which $\Delta G$ is lower can be produced. The inventors developed mathematical models incorporating this knowledge by solving multiple simultaneous equations using thermodynamic data to predict concentrations of products that would result. These models include competition for substrates and intermediates.

This work was undertaken to understand and mathematically model fermentation in the cow's rumen. However, this basic research led to applied research discoveries and inventions related to biofuel production. The inventors developed a process called "directed equilibrium". Considering a system that can make many different products, if these products are limited by thermodynamics, one can add undesired compounds to the media and make it thermodynamically infeasible to produce more of those undesired compounds. Thus, only the desired products will be made, and only organisms that make the desired compounds will survive. If it is not possible to find conditions to specifically favor a certain desired metabolite, one can also use enzyme inhibitors to shut off undesired pathways that are difficult to manipulate by thermodynamics. Thus, it is possible to control at least some of the products or reactants in the system to direct the system to a different equilibrium. In this way, the inventors have been able to discover several useful microorganisms for different industrial processes.

Directed Equilibrium Process

The inventors calculated the change in free energy ($\Delta G$) for many different reactions in different fermentation systems and found that after accounting for some energy for ATP synthesis, the $\Delta G$ was near 0 for the interconversion among many end products. The calculations further showed that some reactions are near equilibrium even with very low concentrations of some products. For example, ethanol was found to be near equilibrium in rumen fermentation even though there is very little ethanol in the fermentation liquid.

This observation showed that the reason for the low concentration of ethanol in the rumen was that it was not a thermodynamically favored product. The inventor concluded that changing the concentrations of other products such as hydrogen or acetic acid would result in greater ethanol concentration. In fact, experiments demonstrated this point.

Once the reason for the low concentration was determined, and the conditions to favor ethanol production were identified, the conditions of the fermentation could be altered to select for organisms that produce the desired alcohol. The isolated microorganisms could be further developed by growing them under conditions in which ethanol production was thermodynamically favored over other products. For example, an organism found to produce both ethanol and acetate can be grown in $H_2$ or CO gas headspace, or with high acetic acid concentration, so that organisms that produce more ethanol and less acetic acid are more fit. Over many generations, the culture selects itself into a culture that produces more ethanol from the gases presented, or a selective process is undertaken in accordance to the invention.

In general, the steps of the Directed Equilibrium process include any or all of the following:

1. Obtain a culture of microorganisms, which includes activity that enables the conversion of a substrate to the desired product.
2. Determine the association of all co-products for all end products for and desired end products based on the stoichiometry of balanced chemical reactions.
3. Calculate the $\Delta G$ for conversion of fermentation substrates to each observed product and the desired product. To calculate the $\Delta G$, determine the $\Delta G°$ for formation of each product and reactant from the elements. These values are typically found in textbooks. The $\Delta G°$ (the free energy under standard conditions) is determined for each reaction based on the stoichiometry of each reaction for conversion of the substrate to each product and the $\Delta G°$ of formation for products and reactants. The $\Delta G$ is determined by adjusting the $\Delta G°$ to the temperature of the fermentation, and using the actual final concentrations for each product and reactant. Although this step can be enormously helpful it may not be necessary to formally calculate equilibrium concentrations or $\Delta G$.
4. Determine alternative conditions that will shift fermentation to thermodynamically favor production of the desired product. These conditions may include inhibitors of pathways that are otherwise favored, or addition of undesired products or gases or removal of desired products or gases. This aspect of the process can be aided by using a mathematical model in a spreadsheet developed as part of the previous step. Alternatively, adding inhibitors to reactions that produce competing products (e.g. use same substrates) or adding concentrations of alternative products will favor production of the desired product. The basis of the response is the fact that the fermentation approaches equilibrium, whether it is calculated or not, so other end product concentrations prevent competing reactions.
5. Incubate the feedstock with microorganisms while maintaining the conditions to shift the fermentation toward producing more of the desired product. This step may require continuous infusion or removal of metabolites or gases to make the desired product thermodynamically favored over other products.
6. Whereas it may be cost prohibitive to continuously maintain conditions to produce the desired product over all other products, microorganisms that produce the desired product will be enriched for over time decreasing future competition for other products. These microorganisms grow faster under the conditions that favor production of the products they make, so diluting all organisms repeatedly overtime results in disappearance of organisms that produce undesired products.
7. An alternative approach to the previous step is to use conditions that favor production of the desired product but which may not result in its accumulation. For example, including an ethanol-degrader in the fermentation and conditions leading to ethanol production and subsequent degradation (e.g. high $H_2$, low $CO_2$) would manage to keep ethanol producers in the culture, and they could be further enriched or cultured in a subsequent step.
8. To select a pure culture of microorganisms to produce mainly the desired product, the enriched culture is diluted serially and plated or a roll tube is produced to grow them in an agar as individual colonies. Thermodynamic conditions (e.g. concentrations and partial pressures of gases) are used so that only the desired organisms can grow. Colonies that grow are selected, purified and tested to use them under conditions wherein they can produce the desired product based on the thermodynamic model.
9. Even a pure culture of a microorganism might produce a wider array of products than desired, or may not produce a high concentration of the desired products. Directed Evolution can be conducted by subjecting the pure culture to fermentation on the feedstock to be digested or substitute feedstock while controlling the products and reactants to make it thermodynamically favorable to produce the desired product over other products. Over many successive generations, as described previously, mutant organisms thrive and other organisms are diluted or washed out.
10. Another aspect of the process includes growing the microorganism with a high concentration of the desired product to select for organisms that can tolerate such a high concentration. Furthermore, conditions can be used to make it thermodynamically favorable to degrade the desired product. Such organisms might be isolated while degrading a compound, and later be grown under different conditions wherein producing the product is thermodynamically favored and under those opposite conditions, the product may be produced.
11. Furthermore, the microorganisms selected can be made more tolerant to the desired product by growing them in the presence of increasing concentrations of the desired product while maintaining conditions to make it favorable to continue producing the desired product in the presence of the high concentration.
12. Another aspect of the invention is to use the second law of thermodynamics to analyze the fermentation system, including an industrial fermentation and each of the organisms in it, to understand what combinations of organisms can digest feeds to certain concentrations of products, and thus understand how to use the optimal organisms for all components of the feedstock available for the products that are desired.

The directed equilibrium process when used to enrich and isolate microorganisms differs from previously known processes in that a microbial system is analyzed using multiple simultaneous equations based on the second law of thermodynamics to develop conditions wherein only organisms that produce a certain product can survive or, at least are more fit than undesired organisms. Previously known systems for isolating microorganisms have used the starting mixed culture and certain substrates to enrich or isolate organisms that could use those substrates, but a wide array of products could result. Often, no organisms that produce the desired product were isolated because the conditions (pH, temperature, gas composition, metabolite accumulation) selects against the desired organisms.

The present invention applies a newly discovered principle, which is not yet widely understood or accepted, that microbial ecosystems approach thermodynamic equilibrium. The inventors discovered this principle and applied it to control microbial ecosystems and enrich and select for microorganisms that produce a desired product. Using mathematical models employing the laws of thermodynamics, it is possible to select and develop microorganisms for many different processes.

Production of Alcohols and Acids from $H_2$, $CO_2$, and CO

One embodiment of the current application is the production of lower alkyl alcohols from $H_2$, $CO_2$ and CO using the directed equilibrium process. Using a ratio of $H_2$ to $CO_2$ or $H_2$ to CO or both determined by thermodynamic analysis to make greater concentration of the desired product possible, and to favor the desired product over undesired product, drives the reaction toward the desired alcohol or desired acid. In this way, a higher concentration of the desired product, and a lower concentration of the undesired product, is obtained and a greater percentage of the gas is converted to the desired product.

In addition, using elevated pressures of the gases, including total pressure greater than 1 atm and preferably greater than 2 or even more preferably greater than 4 atm, makes the synthesized products (e.g. ethanol) thermodynamically more favored than degradation of the products back to gases. Increasing pressures also shifts fermentation toward alcohols over acid production, and toward longer chain-length of acids (e.g. butyrate or valerate) and longer chain-length of alcohols (e.g. butanol).

The pH in the process is controlled to optimize microbial growth and conversion efficiency to alcohols. For example, pH 5 favors alcohol production over acid production more than pH 7 with other conditions being equal, but at pH 5 microbial growth may be decreased. Depending on the conditions and organisms, alcohol production may best be achieved at pH from about 4 to about 7, or even lower than 4.

The inventors were able to isolate microorganisms that could synthesize alcohols and volatile fatty acids from $CO_2$, CO and $H_2$. In the process, the concentrations of infused gases and other products are adjusted to ratios that make production of the desired products thermodynamically favorable, and partial pressures are increased, so that high concentrations by volume of the desired product can be produced. For example, ethanol was produced in media with greater than 10% ethanol concentration by volume.

Second, the adjustment in gases and other metabolites increases the percentage of the infused gases that is converted to the desired product. A higher partial pressure of $H_2$ relative to $CO_2$ or CO favors greater conversion of gases to alcohols rather than acetic acid. For example, under certain conditions ethanol production is thermodynamically feasible while acetate production is not, and ethanol is formed with little production of acetate.

Third, microorganisms that are used for this process, isolated as an aspect of the present invention, were found to increase the percentage of gases converted to the desired product compared to existing microorganisms, and these isolated microorganisms have greater tolerance to the desired product. Some isolated microorganisms produced ethanol from $CO_2$ released from biomass digestion and added $H_2$ to greater than 7% ethanol by volume. Other isolated organisms produced ethanol, 1-propanol and/or 1-butanol from added $CO_2$ and $H_2$ in media with 10% ethanol, and were tolerant and grew in media with as much as 10% ethanol, 6% 1-propanol, or 6% 1-butanol.

Fourth, these improvements and the isolated microorganisms also increase the rate (i.e. unit product per liter per unit time) in which the desired products can be produced.

Fifth, in addition to production of acetate and ethanol, longer chain alcohols and acids can also be produced from the synthesis gases. For example, some isolated organisms and processes predominantly produced butyrate rather than acetate. Some isolated microorganisms produced significant amounts of iso-butyrate and iso-valerate from $CO_2$ and $H_2$ or CO and $H_2$. Rumen microorganisms are known to make longer-chain carboxylic acids including odd-chain length carboxylic acids. The inventors are making caproic acid ($C_6$), caprylic acid ($C_8$), capric acid ($C_{10}$) or longer carboxylic acids as well.

Sixth, microorganisms may be improved through a process of directed evolution described as an aspect of the present invention. These improvements pertain to producing more of a desired product as a fraction of all products, at a higher concentration, and at a higher rate per unit time.

Another aspect of the invention includes using mixed cultures of microorganisms that can produce one or many different products. These may be undefined cultures or mixtures of pure cultures.

Some industrial processes produce low concentrations of the synthesis gases among other gases like nitrogen or air. By adjusting the ratio of $CO_2$, CO and $H_2$, or increasing total gas pressures, these relatively low concentrations can be used more effectively for synthesis of desired compounds. In fact, simply increasing the total pressure makes it possible to produce products from residual gases from industrial or agricultural processes that would otherwise be discarded. For example, 1% $H_2$ could be used in this process more easily than it may be recovered for other use.

These improvements to methods to make alkyl alcohols from gases, adjusting ratios of gases and increasing pressure, increase alcohol or acid concentrations when using cultures of microorganisms that have already been isolated and may or may not already be considered for industrial production of acids or alcohols. These improvements also increase the portion of gas converted to the desired substrate.

Using microorganisms isolated from the rumen of a cow, but which could be isolated from many other environments, allows for production of alkyl alcohol at greater concentration of ethanol or other alkyl alcohol than previously disclosed. The microorganisms already isolated, and that can be isolated, are an aspect of this invention. Methods to isolate the microorganisms that can be used for this process are another aspect of the invention.

Process to Calculate Free Energy and Equilibrium Concentrations

A mathematical model defined in a spreadsheet is used to determine the change in free energy for different reactions that may occur in fermentation. The model may be modified by adding or subtracting reactions as warranted by different types of fermentation. In addition, the free energy change for reactions can be determined for different conditions (e.g. temperature, pressure, pH, concentrations of metabolites, pressures of gases). In addition, the equilibrium concentrations or equilibrium ratios of metabolites can also be determined. The description that follows provides the information necessary to create the model, or a similar model for different metabolites that can be included.

The balanced reactions giving rise to each potential product from the biomass source are first determined. For example, acids, alcohols and alkanes like methane can be derived ultimately from $CO_2$ and $H_2$. The stoichiometry is determined by balancing each reaction so that equal numbers of carbon, hydrogen, oxygen and so forth are on each side of the equation.

For example, $$CO_2 + 4H_2 \leftrightarrow CH_4 + 2H_2O$$

$$2CO_2 + 4H_2 \leftrightarrow CH_3COOH \text{ (a.k.a. acetate)} + 2H_2O$$

$$3CO_2 + 7H_2 \leftrightarrow CH_3CH_2COOH \text{ (a.k.a. propionate)} + 4H_2O$$

$$4CO_2 + 10H_2 \leftrightarrow CH_3CH_2CH_2COOH \text{ (a.k.a. butyrate)} + 6H_2O$$

$$2CO_2 + 6H_2 \leftrightarrow CH_3CH_2OH \text{ (a.k.a. ethanol)} + 3H_2O$$

$$3CO_2 + 9H_2 \leftrightarrow CH_3CH_2CH_2OH \text{ (a.k.a. 1-propanol)} + 5H_2O$$

$$4CO_2 + 12H_2 \leftrightarrow CH_3CH_2CH_2CH_2OH \text{ (a.k.a. 1-butanol)} + 7H_2O$$

$$CH_3COOH \text{ (a.k.a. acetate)} + CO_2 + 3H_2 \leftrightarrow CH_3CH_2COOH \text{ (a.k.a. propionate)} + 2H_2O$$

$$2CH_3COOH \text{ (a.k.a. acetate)} + 2H_2 \leftrightarrow CH_3CH_2CH_2COOH \text{ (a.k.a. butyrate)} + 2H_2O$$

$$CH_3COOH \text{ (a.k.a. acetate)} + CH_3CH_2COOH \text{ (a.k.a. propionate)} + 2H_2 \leftrightarrow CH_3CH_2CH_2CH_2COOH \text{ (a.k.a. valerate)} + 2H_2O$$

Thus, the balanced equations can be determined even without knowledge of the exact pathway. The respective pathways are determined for any and every reaction thought to occur in the fermentation system of interest. Which reactions occur can be assumed based on what products accumulate or are otherwise found in the fermentation.

The $\Delta G$ for any pathway depends on which products and reactants are produced, and therefore different conditions are needed to make each reaction thermodynamically feasible. The change in Free Energy under standard conditions ($\Delta G°$) is determined in the established way of calculating the Free Energy of Formation from the basic elements for each reactant and product and subtracting the Free Energy of Formation of the products from the Free Energy of Formation of the reactants (Chang, R. 1981. Physical Chemistry with Applications to Biological Systems: Second Edition, MacMillan Publishing Co., Inc., New York, which is incorporated herein by reference). For the current patent application, the free energy of formation values not found in the book authored by Chang were obtained from the literature (Guthrie, J. Peter; 1992. A group equivalents scheme for free energies of formation of organic compounds in aqueous solution. Canadian J. Chemistry 70:1042-1054 which is incorporated herein by reference). The relevant values from the literature are provided again in Table 1. Similar information can be obtained from these references and others if desired to add other metabolites to the model.

The values in Table 1 are the relevant thermodynamic data under standard conditions for these reactants and products as well as some other important potential fermentation intermediates. These values represent the free energy of formation ($\Delta G°$) and enthalpy of formation ($\Delta H°_f$) of the metabolites from the elements (e.g. $H_2$, $O_2$, graphite). Free energy ($\Delta G°$) and enthalpy ($\Delta H°$) under standard conditions and concentrations can be determined from these tabular values for each reaction of interest (Chang, 1981 as cited). Standard conditions are 1 M concentration of each soluble reactant and product, $1.01325 \times 10^5$ Pa (1 atm) of all gases, and 298.15 K.

$$\Delta G° = \Delta G°_f \text{ of products} - \Delta G°_f \text{ of reactants, and}$$

$$\Delta H° = \Delta H°_f \text{ of products} - \Delta H°_f \text{ of reactants}$$

Adjustment to each $\Delta G°$ for temperature can be made using a transformation of the van't Hoff equation and enthalpy where $T_1$ and $T_2$ are the initial and final temperatures respectively, and $\Delta G°_{T1}$ and $\Delta G°_{T2}$ are the respective standard free energy values:

$$\Delta G°_{T2} = T_2/T_1 [\Delta G°_{T1} - \Delta H°(T_2-T_1)/T_2]$$

So, for example the $\Delta G$ at 39° C. or 312 K was determined for many of the reactions of interest from the tabular data reported at 298.15 K because the fermentations were conducted at 312 K.

Once the $\Delta G°$ is determined, it can be used to calculate the actual $\Delta G$ for a specific set of conditions using the equation:

$$\Delta G = \Delta G° + RT \ln\{[\text{products}]/[\text{reactants}]\}$$

where the [products] and [reactants] are concentration of all products or reactants in the fermentation, T is temperature in degrees Kelvin. For the current studies temperature was usually set to 312 K. R is the gas constant=0.00831 kJ/K. Given the value of $\Delta G$, the free energy available for a reaction can be shown. If the $\Delta G$ is negative, there would be energy for organisms to produce ATP and grow while carrying out the process. If the $\Delta G$ is positive, the opposite reaction might enable organisms to obtain energy. Generally, about 44 kJ/mol is required for fermentation organisms to produce a mole of ATP, but many organisms and reactions can produce a fraction of an ATP and the exact requirement for free energy depends on energy status of the organisms and other factors.

TABLE 1

Thermodynamic data of selected compounds.

| Substance | $\Delta H°_f$ | $\Delta G°_f$ |
|---|---|---|
| Methane (g) | −74 | −50 |
| Ethane (g) | −84 | −32 |
| Methanol (aq) | −201 | −176 |
| Ethanol (aq) | −235 | −182 |
| 1-Propanol (aq) | −255 | −255 |
| 2-Propanol (aq) | −273 | −186 |
| 1-Butanol (aq) | −275 | −163 |
| 2-Methyl-l-propanol (aq) | −284 | −167 |
| 2-Butanol (aq) | −293 | −179 |
| 1-Pentanol (aq) | −293 | −179 |
| Acetoaldehyde (aq) | −294 | −153 |
| Acetic acid (aq) | −432 | −394 |
| Propionic acid (aq) | −453 | −385 |
| Butyric acid (aq) | −475 | −378 |
| Valeric acid (aq) | −491 | −365 |
| Caproic acid (aq) | −511 | −386 |
| Glucose (aq) | −1264 | −917 |
| $CO_2$ (aq) | −413 | −386 |
| $H_2$ (g) | 0 | 0 |
| Water (l) | −286 | −237 |

Free energy in kJ per mole under standard conditions of several potential fermentation metabolites at 298.15 K and $1.01325 \times 10^5$ Pa (1 atmosphere). Standard conditions are 1 M concentration of each soluble reactant and product, $1.01325 \times 10^5$ Pa (1 atm) of all gases, and 298.15 K.

The inventors have taken the thermodynamics of fermentation to a whole new level. They discovered that using actual concentrations of reactants and products, many of the metabolites in fermentation are near equilibrium with each other, or ΔG values are close to 0 for the presumed interconversion of the end products. The explanation is that as one metabolite builds up, there is less energy that can be obtained by making more of that metabolite. Less energy means less ATP or microbial growth supported. Therefore, less of that product is made. This knowledge enabled the inventors to determine conditions that are necessary to select for previously unknown microorganisms carrying out previously unknown pathways such as synthesis of medium-length carboxylic acids and alcohols from $CO_2$ and $H_2$.

All of the separate equations for ΔG are compared for a given set of conditions, and the conditions altered in a spreadsheet to determine the impact on the ΔG for each reaction. In this way, conditions can be determined in which a desired reaction is favored (ΔG more negative) compared to other reactions.

In addition, the equilibrium concentrations of products are determined assuming certain reactions might go to equilibrium and use available substrate. For example, in a mixed culture fermentation including methanogens, with $H_2$ pressure set high and $CO_2$ pressure set low, degradation of VFA to $CH_4$ and $CO_2$ would be favored over VFA production from $CO_2$ and $H_2$. Using the thermodynamic model requires the understanding that selection for conditions to accumulate a favored product are not necessarily the same as conditions to enrich for or select organisms that make that product. It may be advantageous to establish conditions in which the favored product is created before it is converted to something else by different organisms. As long as conditions favor production of the desired product in the first place, they may be ideal for enrichment or isolation.

The equations are entered into a spreadsheet to solve simultaneously for several different potential reactions. In addition, several different sets of conditions can be compared to determine what conditions are necessary to shift fermentation from one metabolite to another. For example, many anaerobic microbial fermentations produce methane from $CO_2$ and $H_2$. By altering the ratio of gases in the digester, one can show ratios and pressures that favor production of acetate relative to methane. The model may show that conditions to inhibit methane may be necessary in a mixed culture, or to show the ratio of gases that favor maximal acetate production.

When a reaction proceeds to equilibrium, the ΔG tends toward 0. The ΔG for the simultaneous equations can be set to 0 or some negative value representing a certain amount of captured ATP (e.g. −44 kJ/mol of ATP generated) or a certain efficiency of a process. The equilibrium model shows whether or not production of a certain product is feasible under a certain set of conditions. For example, the conditions necessary to produce a certain concentration of ethanol from $CO_2$ and $H_2$ can be calculated. It is especially advantageous to use the integrated model to determine the potential to produce a desired concentration of ethanol in the system in which the soluble $CO_2$ and $H_2$ may be limited by the competing pathway to produce acetate from the gases. The equilibrium model integrating multiple reactions can show the conditions necessary to shift fermentation from acetate to ethanol. The simplest way to calculate these conditions is to determine the ΔG for a stoichiometrically balanced conversion of acetate to ethanol, and then set the ΔG to 0 and solve for the ratio of ethanol:acetate under different conditions. Using the equilibrium model, it is possible to show a set of conditions wherein the acetate cannot be further concentrated but the ethanol can be concentrated above 10% by volume of the media. Thus, the integrated model establishes conditions to isolate organisms or to use isolated organisms to produce a high concentration of ethanol or to shift from acetate to ethanol production.

The free energy of individual reactions is determined in chemistry and is occasionally used for industrial fermentation reactions. However, the inventors use these calculations in a far more sophisticated way integrating multiple reactions to determine conditions to shift fermentation from one product to another.

Methods of Microbial Enrichment and Isolation

Once having established the conditions that make production of a certain product thermodynamically feasible or thermodynamically favorable compared to other possible reactions, conditions are established to favor production of certain products. These conditions are maintained for production, and they are used to enrich for certain microorganisms that produce the desired products, and to isolate the organisms that produce the desired product.

The organisms selected and developed are robust (easily maintained and grow quickly), produce the desired products (e.g. alcohols and acids) at a high rate to a high concentration of product, and convert a high percentage of the substrate (e.g. gases) to the desired products. In general, isolation methods employ mathematical models incorporating thermodynamics and kinetics to create conditions in which only the desired organisms can grow.

Standard Microbiological Procedures

Generally, microbial selection is preceded with enrichment of desired traits. Organisms that have desired functional traits are enriched under specific conditions for several periods of growth followed by sub-culturing and dilution. For example, conditions can be created that favor long-chain acid production so that only the long-chain acid producers grow quickly. Selective media are inoculated with a mixed culture and incubated under those conditions for one to five days. Even longer lengths of time can be used to select slower growing organisms. A culture starting with $10^8$ viable cells per ml may end with $10^{10}$ cells per ml, and 99% of the new cells will have grown recently under the restrictive conditions. Therefore if a rare organism in the original culture thrives under highly restrictive conditions, it will dominate the new culture. For example, one in a million organisms, or 100 in a hundred million, could make up 99% of the culture after one enrichment phase if only those organisms can grow. If the conditions only favor desired organisms, but do not completely exclude competitors, it takes several iterations of culturing and sub-culturing to reach a steady state in which more organisms with the desired traits exist in the culture compared with the initial conditions. The inventors typically use a few to more than 10 separate enrichment steps.

Often different conditions are used in alternating enrichment steps. One set of conditions may be used to select for a certain functional trait, and a second set of conditions used sequentially for a second functional trait. For example, if we desire organisms that produce alcohols we may use one set of conditions to select for alcohol production from gases and a second set of conditions for production of alcohols from cellulosic biomass. The result will be organisms that can produce alcohols from both gases and cellulosic biomass Once the desired traits have been enriched, individual isolates of the organisms are selected. Serial dilutions from 1 to $10^{-14}$ are poured to agar plates, which are incubated under restrictive conditions. The inventors incubate agar plates with specific gas compositions and pressures. The inventors also use roll tubes at times to apply certain types of gas composition.

For roll tubes, warm agar is inoculated in test tubes, which are sealed and rolled on ice to make the agar gel. The agar hardens around the perimeter of the tube. Both agar plates and roll tubes typically are incubated at 40° C. until discernable colonies form, usually within one to three days. Higher or lower temperatures can also be used to obtain organisms that thrive at different temperatures.

Colonies are picked from the tubes and plates using sterile technique. The plates and tubes with less diluted inoculation have overlapping colonies, while the ones that are highly diluted do not have any colonies. Some plates have individual colonies, and these are added to a broth and incubated under conditions to favor production of the desired product. The inventors used 32-liter canning pressure cookers as anaerobic chambers. Several racks of test tubes or agar plates can be added to the chambers with adequate headspace so that gases do not need to be changed more than once a day. The chambers support up to 3 atmospheres of gas infused through a valve into the chamber. In addition, the leading organisms were incubated in tubes or flasks with gases bubbled into each fermentation using small aquarium pumps inside the chamber.

The products each microorganism isolate produces may be screened using rapid procedures (e.g. pH after titration to a specific point with sodium hydroxide to determine total acid produced, or optical density to estimate microbial growth), and leading candidates are analyzed for several products using gas chromatography (GC) or other technique. After an initial screening of all isolates, the most promising isolates are further evaluated by determining the optimal conditions for their growth (e.g. pH, temperature, substrates, oxygen), and the rate of growth (g/L per day), sensitivity to end products (e.g. acids, alcohols).

Following this process typically isolates and evaluates a few hundred to a few thousand organisms each run. The results are evaluated to determine which end products and metabolic pathways dominate among the favored isolates and potential weaknesses of the isolated microorganisms for use in an industrial process. Once the best cultures are selected and evaluated under many different conditions, the growth rate, production rate, conversion efficiencies (percent of $CO_2$ and $H_2$ conversion to different products), titer and tolerance to potential end products are determined.

After evaluation of the leading isolates and identification of the weaknesses of each leading isolate, a process of mutagenesis can be initiated. In this process, the conditions in which the desired products are strongly favored are used on separate pure cultures of large numbers of organisms (e.g. $10^{10}$) of an isolate. Conditions are established in which production of desired products are favored and production of undesired products are strongly disfavored. For example, if an organism only produces a few products, the inventors can focus on the conditions to select against those few undesired products. A range of conditions can be used to both favor desired organisms and disfavor undesired ones. No organisms grow under many sets of conditions, while under other conditions a few grow and they take over the culture. The survivors can then be enriched again under even more restrictive conditions. In this way, the mutants that have special abilities within the originally pure culture can survive. To increase the genetic diversity, some cultures are exposed to different levels of ultraviolet light briefly at the beginning of the incubation. The treatment increases mutation rate and accelerates the evolutionary process. The developed organisms are selected on agar plates and tested as previously. Thus, the entire process of enrichment and selection can repeated if necessary many times for both original selection and development.

Much of the emphasis in recent years has been on specific genetic manipulation and transformation to engineer organisms. However, isolation and non-specific mutation methods are also important especially in the early stage of microbial development. First, the genotype of the newly isolated organisms is not known, and in many cases plasmids or other vectors may not have been identified. Second, the types of changes that are desired may not be understood metabolically. For example, isolating organisms that are tolerant to high concentrations of the desired products (e.g. specific acids), and grow quickly or at least are robust are complex problems. These traits are complex and may require several genetic changes, many of which are not fully understood. Therefore, it would not be easy to begin specific manipulations of DNA to create the desired organism. Furthermore, the inventors discovered it is often not necessary as there are many organisms that already evolved to thrive under the conditions needed in an industrial process. Therefore the inventors initially focus on enrichment, isolation and nonspecific mutation for obtaining organisms with the traits that are difficult to engineer, and then apply specific engineering to simpler DNA modifications later if necessary. For example, the inventors selected organisms that convert a high percentage of the gases to the desired product, and isolated organisms that produce differing amounts of desired products under certain conditions; the organisms can obtain energy from producing the desired products. If necessary, some of these organisms can be further manipulated through specific genetic engineering to knock out the ability to produce undesired products later. Once organisms are transformed, mathematical models can again be used to select for the successful individuals and to establish conditions that maximize the production of the desired products from reactants.

Use of Mathematical Models

The inventors developed transformational improvements to microbiological methods based on mathematical models of fermentation. The inventors use integrated models that simultaneously use both thermodynamics and kinetics, and that solve simultaneous equations representing multiple pathways. For example, the approach predicts the consequences of competition for substrates, and determines conditions in which organisms that obtain energy from a certain pathway are or are not be able to grow. The mathematical models can be quite complex and all possible results cannot be presented here. However, all the information needed to recreate the models for production of any fermentation product is presented in this application, and general conclusions from the models will be described below to illustrate the process for production of alcohols and carboxylic acids from $H_2$ and $CO_2$.

One illustration relates to the Gibbs free energy change ($\Delta G$) for different reactions that can produce products from $CO_2$ and $H_2$. If the $\Delta G$ is negative, the reaction can proceed in the forward direction spontaneously. The most negative $\Delta G$ represents the reaction with the most favorable conditions to carry out the reaction. Reactions with positive ΔG can proceed in the forward direction, but only if energy is put into the system to drive the reaction forward. In other words, another linked reaction with an even greater absolute value of ΔG that is negative must be linked to make the overall ΔG negative. For end products relative to reactants like $CO_2$ and $H_2$, a positive ΔG means the organisms that carry out the reaction will have to use their own energy to make the reaction proceed. If an organism is using energy to make the desired product, it will not be able to grow from carrying out the reaction. On the other hand, an organism that carries out a reaction under conditions with very strongly negative ΔG will not only be able to carry out the reaction without using its energy stores, it will also be able to link ATP generation or other storage of energy. Thus, the strongly negative ΔG will allow for the fastest growth rates (particularly with some types of organisms because the energy can be generated from dissipation of proton gradients in continuous fractions of ATP).

The inventors used this model to enrich and isolate organisms that produced carboxylic acids or alcohols in a high concentration and did not produce as much acetic acid when it was not desired. The calculated ΔG depends on the ratio of products to reactants, and the inventors calculated the ΔG for several different potential pathways. There are changes to the fermentation that strongly change which products are favored from $H_2$ and $CO_2$. One change is the ratio of $H_2$ to $CO_2$, and another change is the combined pressure of both gases. The ratio of $H_2$ to $CO_2$ that produces the highest possible concentration of acetic acid is 2:1, but the ratio to produce the highest concentration of alcohols is 3:1. Carboxylic acids with greater than two carbons are produced in the highest potential concentration with ratios of $H_2$ to $CO_2$ between 2:1 and 3:1 with the longer acids favoring the higher ratio. The optimal ratio to convert acetate to propionate is 3:1.

Increasing the total pressure of $H_2$ and $CO_2$, especially at the optimal ratio, exponentially favors alcohols and long-chain acids over acetate. For example, at twice the pressure (2 atm vs. 1 atm) the equilibrium concentration of acetate increases 70 fold, but the equilibrium concentration of ethanol increases more than 250 fold. Thus, incubation under moderate pressures of optimal ratios of $H_2$ and $CO_2$ shifts equilibrium toward desired products and in fact, the organisms that produce those products will be favored. High ratio of $H_2$ to $CO_2$ also favors longer-chain carboxylic acids over acetate. For example, at twice the pressure of total gases, the concentration of butyrate increases 17,000 fold (compared to 70 fold for acetate), and the equilibrium concentration of butanol increases 80,000 fold. The large numbers and huge swings in directionality of reactions make it necessary to perform the calculations in order to define the conditions for synthesis of the desired compounds. It is not surprising that previous investigators may have occasionally observed butyrate or butanol in fermentations without being able to repeat or confirm the observations. The conditions making it thermodynamically favorable to make these products must be understood in order to repeatedly and reliably produce the products. These procedures have been tested and used already and the empirical results confirmed the theoretical expectations.

In addition to these procedures to favor organisms that produce these desired products, the metabolic models the inventors are using point to several other ways to further select desired organisms. One surprising approach to obtain organisms that carry out a desired conversion reaction (e.g. A→B) is to isolate organisms that carry out the reverse of the desired pathway (e.g. B→A). In other words, one can enrich them under conditions that start with a high concentration of the desired product and favor degradation of the product. In a subsequent enrichment phase, the desired product is removed and the thermodynamic conditions are reversed. The resulting organisms can create the desired product under one set of conditions and degrade it under another set. This approach applied to enrichment of organisms selects for a high degree of tolerance to the desired product (only organisms that grow in a high concentration survive) and a high specificity of production (selected organisms have the enzymes to make or degrade the desired product). It is based on the theory that all catalysts decrease activation energy of reactions, and they do not change the equilibrium constant or ΔG. Catalysts such as enzymes accelerate the rate of reactions when those reactions are kinetically controlled, but they must also accelerate the rate of the reverse reactions to an equal proportion. Otherwise the equilibrium constant would change. A corollary to this principle is that all catalyzed reactions are bi-directional. If we seek enzymes to catalyze a given reaction, for example to produce butanol, organisms that degrade butanol have those enzymes. The cell machinery may not be set up to allow the organisms to grow (produce ATP) under both sets of conditions, but many organisms can obtain energy by metabolizing the reaction in either direction.

A further application of the model to establish conditions for enrichment pertains to using aerobic conditions in the enrichment phase. Many organisms can aerobically catabolize a substrate like glucose to $CO_2$ and $H_2O$. However, they may also survive under anaerobic conditions by making another end product that does not require oxidation. For example, they may make acetate and $H_2$ or ethanol or lactate. If oxygen is returned to the environment, they may further oxidize these "end products" to $CO_2$ and $H_2O$ for additional energy. Thus, it is advantageous to isolate such facultative aerobes by growing them in the presence of oxygen and high concentrations of the desired product. For example, the inventors used this technique for isolation of facultative aerobes that produced alcohols from $H_2$ and $CO_2$. In one phase of the enrichment, the alcohol was oxidized to $CO_2$ and $H_2O$, and in the other phase, organisms were grown under conditions to favor production of the desired acid from $H_2$ and $CO_2$. There are special advantages of facultative aerobes. They can be grown aerobically very quickly while only producing $CO_2$ and $H_2O$, which can be easily removed. Even facultative anaerobes are advantageous because of their ease of handing in the laboratory and industrial process.

Methods of Producing Organic Products

Whether using an isolated pure culture of one or more microorganisms or using an undefined mixed culture, the directed equilibrium process allows for production of a desired product in a higher yield relative to other products, at a higher concentration before showing signs of apparent intolerance to end product, and at a consistently high rate. In this process, the thermodynamics of all possible pathways in the fermentation are determined and the conditions are established to favor the desired pathways and produce the desired product. This process goes beyond the calculation of the thermodynamic feasibility of producing one desired product.

All of the products, desired and undesired are included in the calculations, and the ΔG for the interconversion of all end products is also calculated even if pathways for interconversion are not known. These ΔG values estimate the feasibility of one reaction relative to a different one, and if more than one product exists, conditions need to be determined to favor the desired product over the undesired one. Conditions are tested to determine the optimal conditions to favor the desired pathway. One calculates whether the desired pathway is feasible or not and whether undesired pathways are infeasible or disfavored. In this way, the optimal conditions are established and used for production of the desired product.

A further aspect of the directed equilibrium process is that the direction of pathways can be reversed by controlling the thermodynamic conditions. For example, a process to produce $CO_2$ and $H_2$ from acetate or longer chain acids can be reversed to produce acetate from $CO_2$ and $H_2$. In many cases the same microbial culture can be used for both directions, but in other cases the conditions to isolate microbes need to be undertaken separately to optimally control the reaction in the opposite direction.

Directed Equilibrium Process to Produce Lower Alcohols and Carboxylic Acids from $H_2$, $CO_2$, and/or CO Microorganisms One aspect of the present invention is a microbial culture that can tolerate high concentrations of ethanol, such as greater than 2% ethanol by volume, and more preferably greater than 6% ethanol by volume, and even more preferably greater than 10% ethanol concentration by volume. The isolated organisms grow in the presence of these high ethanol concentrations, and convert a high percentage of the gases $CO_2$, CO and $H_2$ to ethanol. The same organisms also tolerate high concentrations of volatile fatty acids, such as 3% total volatile fatty acids by volume or preferably 4% or more preferably 5% VFA by volume. The organisms are also tolerant to low pH, such as less than pH 5 and preferably less than pH 4. However, the organisms generally also grow at neutral pH such as pH 7 or higher. In addition, some of the isolated organisms are tolerant to 6% 1-propanol by volume or 6% 1-butanol by volume, and they make these alcohols when these concentrations of alcohols are present.

In addition, some isolated organisms can produce other products besides alcohols from synthesis gases. These products include acetate and longer-chain acids like propionate, and butyrate. The organisms tolerate high concentrations of the end products. Certain isolates specialize in producing alcohols like ethanol, while others primarily produce a certain VFA like butyrate from the synthesis gases. It is not necessarily advantageous to isolate or develop microorganisms that produce many different products. If many different products are produced, certain products may inhibit further fermentation, and it is more difficult to separate several products. Thus, one advantage of the isolated microorganisms that comprise an aspect of this application is that many isolated isolates specialize in producing few products. For example, they mostly produce alcohols or only short-chain volatile fatty acids (VFA) or mostly longer chain carboxylic acids. The inventors contemplate methods for isolating organisms that produce any particular carboxylic acid or alcohol for use in a specific process.

The present invention pertains to microorganisms that produce high concentrations of alcohols or desired carboxylic acids from gases, a combination of $CO_2$ and $H_2$ or CO and $H_2$ or a combination of all three. Most organisms that were isolated to use $CO_2$ and $H_2$ produced a similar profile of products from CO and $H_2$.

The inventors isolated microorganisms that could produce a high concentration of ethanol from $CO_2$ and $H_2$ or from CO and $H_2$. For example, several isolates were shown to produce ethanol in media with greater than 10% ethanol by volume under conditions that favor ethanol production. These same isolates also produced ethanol when ethanol was not present in the fermentation medium. Surprisingly, when isolates that produce both acetic acid and ethanol were incubated with 6% or 10% ethanol, additional ethanol was produced at a faster rate and as a greater fraction of products (e.g. ethanol over VFA) than when the same organisms were incubated without ethanol at the start. It appears that high ethanol concentration actually inhibits production of acetic acid and other acids.

Some isolates convert a high percentage of synthesis gas to ethanol instead of VFA, and under conditions described as an aspect of this invention can shift metabolism toward even greater ethanol production. Other isolates produce high concentrations of specific VFA. For example, one isolate produces 95% acetic acid (as a molar percentage of all VFA) from synthesis gases, while another isolate produced 48% butyrate, 6% propionate, and 6% isovaleric acid and less than 37% acetate even when incubated under the exact same conditions as the isolate producing only acetic acid.

Most of these isolated organisms grow on glucose or other sugars as well as on gases. Most isolates grew rapidly at pH 7 and continued to grow when the pH was less than 5. Most isolated isolates could grow in media with VFA concentrations exceeding 3% by volume (e.g. 1% of each acetate, propionate and butyrate) at either pH (5 or 7). Some of the isolates could tolerate or utilize $O_2$. The organisms generally grow rapidly and produce the acids and alcohols under strictly anaerobic conditions. The organisms grew rapidly at 40° C., but also grew at lower temperatures and higher temperatures such as 25° C. or 55° C.

Some isolated organisms could degrade biomass comprised of cellulose and hemicellulose to produce alcohols or acids and $CO_2$ and sometimes $H_2$. These same microorganisms took up $CO_2$ and $H_2$ released from the biomass degradation to produce additional alcohol or acid. In some cases, microorganisms that produced mostly ethanol when digesting biomass were recently discovered to also produce ethanol from $CO_2$ and $H_2$. Some of these microorganisms produced mostly ethanol, not other acids or products, and they continued to produce ethanol when the ethanol concentration exceeded 7% of volume. Hydrogen gas may be added to increase the use of $CO_2$ produced from biomass digestion that is subsequently assimilated into additional ethanol. For example, an organism that produces ethanol from cellulosic biomass also produced $CO_2$. When $H_2$ was added to the fermentation, the organism assimilated the produced $CO_2$ and the added $H_2$ into additional ethanol. Thus, more than two thirds of the carbon in the biomass was converted to ethanol.

In addition to using mono-cultures of microorganisms, mixed cultures can also be used. In some cases, the isolates from the mixed culture may have included more than one isolate together (co-isolates), or separately isolated organisms can be combined (co-cultures). The production of certain products sometimes decreases when isolates are further purified by isolating colonies from the culture. It may be that more than one form share the needed activities. Nonetheless, the microbial cultures can be transferred, maintained and grown for long periods of time whether co-isolates, co-cultures or mixed cultures.

In addition to defined and isolated co-cultures, undefined mixed cultures may be used. The advantages of mixed cultures are that fewer micronutrients may be required because some isolates can transfer nutrients (e.g. vitamins) to others, and different products may be produced because a product may be exported from one isolate and taken up by another one. The advantage to undefined mixed cultures is that sterile procedures would not be needed. Mixed cultures could come from the rumen of a cow, the hind but of an insect, compost or soils, among many other sources.

Sources of Microorganisms

The rumen microbial ecosystem, like many other microbial cultures, contains many microorganisms and pathways resulting in a broad array of activity. The end result of this activity normally is determined by the second law of thermodynamics, but the profile of products can be altered by adding metabolites or inhibiting certain pathways. Further, the end products can also be manipulated by the complete removal of certain pathways by isolating specific organisms, using inhibitors with isolates, or genetically modifying organisms. The microorganisms can be undefined cultures or isolated cultures used individually or in mixed cultures to produce the desired activity for biofuel production. For example, ethanol can be produced by rumen microorganisms, but it normally isn't because the organisms favor production of acids rather than ethanol under natural conditions. With different conditions, ethanol can be favored, and the organisms that produce it can be enriched and selected for.

Although any anaerobic fermentation may be an adequate source of microbes, the rumen of a cow is especially advantageous. The rumen is consistently warm favoring rapid metabolism and hosting $10^{10}$ organisms per ml. The high dilution rates wash out organisms that do not grow quickly. These conditions are similar to anaerobic digesters to be used for the proposed process. The rumen gas phase is largely comprised of carbon dioxide and methane with enough hydrogen to make it thermodynamically feasible to produce carboxylic acids. Rumen microbes produce several liters of $H_2$ per day and much more $CO_2$ and these gases are transferred among microbial species and incorporated into methane and carboxylic acids. The mixed culture rumen microorganisms are well known to produce acetic acid from $CO_2$ and $H_2$, and these microbes also convert acetic acid to other volatile fatty acids by incorporating $CO_2$ and $H_2$ to produce propionic acid, butyric acid, and longer chain acids. Rumen microbes are also well known for production of ethanol although ethanol does not accumulate in the rumen because it is subsequently converted to other products. Microbes may be removed from the rumen of a cow by taking them directly from a fistula inserted into the cow's side. Additionally, microbes can be obtained using a stomach tube, or they may be obtained from a slaughterhouse. Microbes may be taken from the feces of a ruminant or from the hindgut as well.

There are many other sources of microorganisms that can be used in place of microorganisms from the rumen of a cow. For example, microbes may be taken from the gut or feces of any other ruminant such as deer, antelope, bison, or camel. They may also be taken from elsewhere in a digestive tract of any type of animal including mammals or non-mammals. Even insects like carpenter ants or carpenter bees or termites host large numbers of microbes that may be suitable. Microbes may be obtained from soils, water bodies, compost, or manure digesters. Fermented foods may also host suitable organisms. For example, wine, cider and beer host organisms that are tolerant to acids and ethanol and that may use and/or produce ethanol.

The following functions can be orchestrated by microbial cultures obtained from a mixed culture such as exist in the rumen of the cow and many other natural and diverse ecosystems. These are functions that may not be observed under natural conditions because of the need to limit some activity that would naturally be present. For example, the production of biofuels or other desired products from synthesis gases, as opposed to production of acetic acid, is as much about limiting enzyme activity as it is about adding it. Isolation of microorganisms can often be used to limit the activity in the system because in nature the metabolites are passed from one organism to the others, thus not providing organisms to pick up the metabolite can enable a desired metabolite's accumulation. This application focuses on the way to effect the following activities using microbial cultures, as well as ways to develop the microbial cultures themselves:

a. Conversion of $CO_2$ and $H_2$ to acetic acid. The acetic acid can be further converted to other VFA or alcohols with the same or other cultures.

b. Conversion of $CO_2$ and $H_2$ to ethanol. The inventors discovered and isolated organisms from the rumen of a cow that convert $CO_2$ and $H_2$ to ethanol.

c. The interconversion of acetic acid and ethanol. The direction of interconversion would be controlled by thermodynamics.

d. Conversion of carbon monoxide (CO) and $H_2$ to acetic acid. This process is a means to use gases produced from high-temperature physical digestion. It is closely related and a part of the pathway for the conversion of $CO_2$+$H_2 \rightarrow$ acetic acid, which is known to be predominant in the rumen. Wherein $CO+H_2O \leftarrow \rightarrow CO_2+H_2$ is a rapid process at moderate temperature, the system that assimilates $CO_2$ and $H_2$ into longer carbon chains also assimilates CO and $H_2$. The inventors discovered that most of the organisms that produce volatile fatty acids or lower alkyl alcohols from $CO_2$ and $H_2$ produce a similar profile of end products from CO and $H_2$.

e. Conversion of CO and $H_2$ to ethanol. Several organisms were isolated from the rumen that could carry out this process.

f. The inventors also contemplate the direct conversion of $CO_2$, CO, and $H_2$ to ethanol without producing acetic acid. Yeast are known to make ethanol by two pathways that both pass through acetic acid, and yet little acetate is released from the cell. These pathways include: acetyl CoA to acetate to acetyl aldehyde to ethanol and alternatively, pyruvate to acetate to acetyl CoA to ethanol. The present application will show a set of conditions that make it thermodynamically favorable to produce ethanol from $CO_2$ and $H_2$ or CO and $H_2$ but not thermodynamically favorable to produce acetate from the gases.

g. Conversion of organic acid to alkyl alcohol. For example, lactic acid conversion to ethanol, or butyric acid conversion to butanol.

h. Conversion of one organic acid to another. For example, acetic acid converted to propionic acid, or acetic acids converted to butyric acids, or further elongation of carboxylic acids, or shortening of carboxylic acids.

i. Conversion of acetic acid to $H_2$ and $CO_2$, which could also include acetic acid degrading organisms. These organisms would be used in combination with a way to make acetic acid degradation thermodynamically favorable such as by purging of gases.

Often more than one function above would be combined. For example, one microorganism may use $CO_2$ and $H_2$ to produce acetic acid (function a), while another one may convert the acetic acid to ethanol or butanol (function c). This combination could result in production of longer-chain alcohols from $CO_2$, CO and $H_2$.

A natural anaerobic or aerobic ecosystem has the enzymes to produce many different products or intermediates, but typically these systems are stable and produce the same profile of products. By selecting for certain enzyme activity and removing others, the desired products can be produced and concentrated.

An efficient way to make acetic acid from waste gases is to maintain a population of reductive acetogens (function a) with high enough pressures of $CO_2$ and $H_2$. Others have proposed adding reductive acetogens to increase acetic acid production in the rumen and decrease methane losses. However, this method does not work in the cow's rumen because the acetogens are already there, and rumen acetate is near equilibrium with $CO_2$ and $H_2$. On the other hand, a digester can increase its total pressure, or the partial pressure of either or both gases to promote the reaction. A culture that does not contain methanogens would naturally make it possible to maintain higher $H_2$ and $CO_2$ pressure than one that contains methanogens, and therefore removing or inhibiting methanogens promotes greater synthesis of carboxylic acids or alcohols from $CO_2$ and $H_2$.

Because the rumen has the microorganisms to assimilate $CO_2$ and $H_2$ into acetic acid, and acetic acid is in equilibrium with ethanol, the pathways are present to convert $CO_2$ and $H_2$ to ethanol.

Desired Characteristics of Microorganisms to Assimilate Synthesis Gases

An aspect of the present invention is the means to obtain pure cultures of microorganisms that can tolerate high concentrations of alkyl alcohols and acids while they produce additional alcohols or acids.

The present application describes the means to enrich for or select microorganisms that can be used to produce products synthesized from gases. The first step to synthesize or enrich for these organisms is to identify the desired physiological traits for the organisms. Understanding these desired traits enables the establishment of conditions where the organisms with those traits thrive The ideal characteristics of desired organisms are as follows:
  Produce desired product or products from gases (CO, $CO_2$, $H_2$)
  Produce desired product or products nearly exclusively
  Produce desired product or products to a high concentration
  Produce desired product or products at a high rate In this case, the desired product may be acetic acid or ethanol, or a microbial culture may be developed to produce a longer chain alcohol or acid from gases, such as propionate or butyrate, or 1-propanol or 1-butanol. For example, microorganisms in the rumen have been shown to interconvert acids like acetic acid, propionic acid, and butyric acid, and to interconvert acids with alcohols. The extent to which these interconversions occur depends on the thermodynamics and the concentrations of various metabolites for the desired pathways as well as competing pathways. Thus, the enzyme activity exists in rumen fluid to convert gases to acetic acid, ethanol, propionic acid, propanol, butyric acid, butanol as well as many other acids and alcohols. The fact that a product occurs in rumen fluid, even at low concentration, implies that at least one isolate of microorganism produces the product. The present patent application describes the means to isolate the desired activity so as to produce the product desired instead of mostly producing other products.

Whatever the product or products desired, the desired cultures of microorganisms should be limited in their ability to produce non-desired products. For example, when using rumen fluid as the microbial culture, under the correct conditions any of several desired products can be produced from $CO_2$, CO and $H_2$, but several different products will result which together may be difficult to separate or may not be desired at a given time. The gases may produce acetic acid and ethanol but these may be interconverted with propionate and butyrate and propanol and butanol. A mixed culture can be controlled to some extent by controlling the fermentation gas mixture and other aspects of concentrations that affect thermodynamics, but several products are likely to be feasible and with too many reaction pathways available it becomes difficult to control which products are produced. In contrast, an isolated microorganism that only produces acetic acid and ethanol can be controlled to some extent by thermodynamics (e.g. higher $H_2$ partial pressure and lower pH increase alcohol over the acid).

If a microorganism is selected that only produces a certain desired product under a specific set of conditions, it will only be able to survive when the thermodynamic conditions are such that production of the desired product will enable it to obtain energy. When the concentration of product is increased, the thermodynamic equilibrium can shift against greater production of the product. The organism may survive by 1) producing a different product, or 2) catabolism (breakdown) of the desired product. It may appear that the microorganism is intolerant to the desired product. However, increasing the concentrations of substrates, decreasing the concentration of other products, or adjusting the ratios of products or substrates can shift the metabolism toward greater product production at even greater concentration of the product. Often, the appearance of intolerance to a product can be overcome this way. One aspect of the present invention is to overcome these apparent intolerances by readjusting products or reactants, especially gas pressures.

At some concentration of product, such as ethanol or acid, the microorganism that produces the product is in deed intolerant to the further concentration of the product even after adjusting for the other product and reactant concentrations. For example, enzymes or cell membranes may be inhibited by the product. Another aspect of the present invention includes isolation and identification of microorganisms that are tolerant to high concentrations of the desired products: ethanol, propanol, butanol, acetic acid, propionic acid, or butyric acid, other alcohol or acid, or a combination thereof. The process to isolate the microorganisms themselves with high tolerance to their products, and the methods to isolate them are both aspects of the invention.

The organisms that comprise an aspect of the present invention are also able to produce the desired products at high rates. The organisms are isolated and screened for such high rates as an aspect of the present invention.

Other characteristics of the microorganisms that may be desired but not required include characteristics that make them easier to handle or more versatile including:

Ability to utilize or tolerate oxygen

Ability to digest biomass including cellulosic biomass

Some microorganisms isolated can digest cellulosic biomass as well as synthesize ethanol from $CO_2$ and $H_2$. Methods disclosed by the inventor in U.S. Ser. No. 61/113,337, which is incorporated by reference were used to isolate organisms that produced ethanol from cellulosic biomass. In some cases, these microorganisms appeared to convert more than 67% of the cellobiose to ethanol, sometimes appearing to convert nearly all of the cellobiose carbon to ethanol when incubated with 2 atm $H_2$. The inventors expected the maximal conversion of carbon to ethanol to be 67% with known pathways producing 2 ethanol per glucose equivalent, and 2 $CO_2$. At the same time, the total gas pressure was found to decrease during the incubation, and the acetic acid concentration sometimes decreased. In one case, the ethanol concentration increased above 7.5% by volume. Thus, conditions for isolation and incubation of microorganisms that were intended to obtain fiber-digesting microbes that could produce ethanol, in some cases, resulted in isolation of microorganisms that could also produce ethanol from $CO_2$ (produced in the fermentation) and added $H_2$. The results were not expected, and in fact they were dismissed until they were found repeatedly for certain microorganisms.

The inventors isolated microorganisms that can assimilate $CO_2$, CO and $H_2$ into ethanol while the concentration of ethanol exceeds 10% by volume. The thermodynamic analysis also suggests that it is feasible to produce high concentrations of ethanol from high $CO_2$, CO and $H_2$ concentrations. At low pressures of these gases, or if the ratio is skewed against the carbon or hydrogen side, it is thermodynamically more favorable to degrade ethanol than to produce it.

The inventors also contemplate microorganisms, and the isolation of microorganisms that can produce propanol or butanol from $CO_2$, CO and $H_2$. The fact that ruminal microorganisms can assimilate acetic acid from $CO_2$ and $H_2$ has been previously reported. The acetic acid is in equilibrium with other acids and alcohols in mixed culture fermentations, including the fermentation in the rumen. Thus, the enzymes and pathways exist for the ultimate production of any of these products from $CO_2$, CO and $H_2$. Microorganisms were isolated from rumen fluid that were tolerant to as much as 6% butanol and which produced butanol from cellulosic biomass. Therefore, pathways are present in rumen microorganisms to produce butanol from biomass, and since these pathways are linked, the entire pathway from gases to butanol is present. The butanol-producing organisms were tolerant to as much as 6% butanol, so producing butanol from $CO_2$, CO and $H_2$ at a similar concentration was contemplated. The ability to also produce propanol at high concentration from $CO_2$, CO and $H_2$ was also logically contemplated similarly.

The inventors discovered that when incubating mixed cultures of rumen bacteria with as much as 6% 1-propanol, 6% 1-butanol, or 10% ethanol under either aerobic or $N_2$ gas phase, the fermentation actively proceeded producing gas from the alcohols. The same enzymes to catabolize alkyl alcohols would be used to synthesize them under $CO_2$, CO and $H_2$ pressures, and these enzymes are present in rumen fluid in organisms tolerant to the alcohols. Organisms that survived these high concentrations of alcohols were found to also produce the alcohols at high concentrations under conditions favoring synthesis of these compounds.

Isolation of Microorganisms

Another aspect of the invention is the discovery that many mixed culture fermentation systems, including the rumen of cattle, have all of the desired activity to produce the desired product. In order to convert a high percentage of the gas to one or more desired products (e.g. ethanol or butanol), the undesired pathways (e.g. acetic acid) need to be prevented. Various inhibitors can be used to slow or shut down undesired pathways. In addition, concentrations of products and reactants can be adjusted to make the desired pathways more favored over the undesired ones. However, when there are many different pathways in a single culture, it can be difficult to end up with only one or two products. Shutting down one pathway often opens another one. A way to limit the number of pathways in the fermentation is to isolate microorganisms with few pathways present from the mixed culture. The various methods used to inhibit undesired pathways (inhibitors or thermodynamics) can be used in the isolation process.

One aspect of the process is to use conditions to control the fermentation to isolate microorganisms that comprise an aspect of the invention. For example, adjustments in gas pressures can be used to enrich and select for microorganisms that are able to produce greater concentrations of desired products (e.g. a specific alcohol or acid) and convert more of the gases to that desired product. Using inhibitors to select against acetic acid production, for example, can also be used to select against acetic acid producers. In this way, organisms can be isolated that produce a high percentage of the desired product, such as ethanol or 1-propanol, because they do not have pathways to produce other products.

The microorganisms that can be isolated to assimilate alcohols and VFA from synthesis gases ($CO_2$, CO, $H_2$) and that would be tolerant to the products they produce, are disclosed as an aspect of this application. These microorganisms continue producing the products even when the concentration is high. The way to manipulate other metabolites to make the high concentrations thermodynamically favorable, and undesired products unfeasible has been disclosed as an aspect of this invention. Using those same conditions to enrich, select and isolate microorganisms that are tolerant to the products is another aspect of the invention. For example, microorganisms can be isolated in the presence of high concentrations of 1-butanol or 1-propanol, and with thermodynamic conditions to synthesize these alcohols from gases (i.e. high partial pressures of the gases at a ratio of 3 to 1 of $H_2$ to $CO_2$). It is thermodynamically feasible to make more of the alcohols even in those concentrations so organisms that carry out the reaction are favored. Alternatively, for a step in the process, microorganisms that utilize the 1-propanol or 1-butanol might be selected by incubating in high concentrations of the respective alcohol and gases that favor degradation of the alcohol (i.e. low $CO_2$ and/or $H_2$). In a subsequent step, these microorganisms can be selected under high $CO_2$ and $H_2$ and optimal ratios so that the organisms that can obtain energy from the opposite pathway are selected.

In general, the unique aspects of the microbial isolation methods for microorganisms that are especially suited for synthesis of alcohols or acids from synthesis gases that are an aspect of the present invention are as follows:

Isolation with high concentrations of the product
Isolation under conditions that thermodynamically favor the product formation
Isolation under conditions that disfavor competing pathways
Thermodynamically disfavor undesired pathways
Inhibitors disfavor undesired pathways
Isolation that favors microbes that grow quickly or produce products at high rates For example, ethanol-tolerant microorganisms that produce ethanol from synthesis gases were selected by growing a mixed culture for many generations in the presence of the gas concentrations that favor ethanol producers more than acetic acid producers. Acetic acid was further inhibited in some cases by growing the cultures at pH less than 5. After enrichment, the culture was diluted to isolate individual colonies that grow from gases as the only energy source (in a ratio favoring ethanol, 3:1 of $H_2$ to $CO_2$), and which may include ethanol in the media. With a different gas mixture, ethanol would be degraded but calculations showed that it would be thermodynamically infeasible to degrade it, even at high concentrations, at high partial pressures and the ratio of 3:1 of $H_2:CO_2$. The same process can be applied to carboxylic acids and other products.

Example Process to Isolate Microorganisms that Synthesize Alcohols from Gases

Several different sets of conditions were used to select for microorganisms that could produce alcohols from $CO_2$, CO and $H_2$. In one approach, conditions that result in degradation of the desired alcohols select for organisms that can also synthesize the desired alcohols or acids. Thus, in some cases conditions were established to enrich or isolate the degraders of products rather than the producers of the products directly. This enabled more specific selection of organisms that were tolerant to a certain product and which had the pathway to make the certain product. For example, microorganisms that degraded 1-butanol to $CO_2$ and $H_2$ also had the enzymes to make 1-butanol from $CO_2$ and $H_2$. On the other hand, an organism that uses $CO_2$ and $H_2$ could make many different products including other alcohols and acids and may not be ethanol tolerant.

Some enrichment and isolation (roll tube) conditions used to enrich and isolate organisms to produce ethanol, propanol or butanol from $CO_2$, CO and $H_2$ are shown in Table 2. For isolations numbered 1 to 6, the enrichment selected for microorganisms that degrade the respective alcohol to gas. Using $N_2$ in the gas phase and high concentrations of the alcohols thermodynamically favored the degradation of the alcohols. Other gases were used in place of $N_2$, including air, $CO_2$ or $H_2$. In the case of air, aerobic or aerotolerant microorganisms were selected. These were easier to handle in some applications. In the case of $CO_2$ and $H_2$, degradation of the alcohols was still favored thermodynamically because of the high or low ratio of $H_2:CO_2$ or $H_2:CO$. Then, isolates were selected that could grow on the gases which were provided in concentrations to thermodynamically favor alcohol production.

Alternatively, in isolations numbered 7 to 8, organisms that could grow on $CO_2$, CO and $H_2$ were enriched, selected and isolated. These organisms produced a number of different products, which were determined through analysis on a gas chromatograph or other procedure. Using a ratio of $H_2:CO_2$ of 3:1, pressure of 2 to 4 atm and potentially moderately low pH (e.g. 4-5) favor alcohols over acids. This combination of conditions can be used to shift fermentation toward alcohols. Previous investigators did not isolate organisms under conditions that made the desired alcohol or carboxylic acid thermodynamically feasible, and especially not thermodynamically favorable compared to other potential products.

In addition to the conditions shown in Table 2, other conditions also work well. For example, the ratio of $H_2$ to $CO_2$ could be higher, such as 10 to 1 or 100 to 1 while it is still feasible to produce some ethanol rather than degrade it. This higher ratio shifts fermentation further in favor of alcohols or longer-chain carboxylic acids over acetic acid, and conditions can be established in which it is only feasible to make ethanol and not make acids. Many of these enrichments were undertaken with 2 to 4 atm total pressure to further shift the fermentation toward alcohols and longer-chain acids. It is also advantageous to include alcohols in the enrichment or in the isolation medium and when the ratio of $H_2$ to $CO_2$ or $H_2$ to CO is near the optimal level, and especially when under greater than 2 atm and preferably greater than 4 atm total pressure. It is still thermodynamically feasible to produce more of the ethanol or desired acid. This inclusion increases selection pressure to obtain more alcohol-tolerant organisms. It is also advantageous to include acetic acid or other VFA in the media during enrichment or isolation as the VFA inclusion shifts equilibrium against further VFA production and also selects for organisms that are tolerant to higher concentrations of VFA. Individual VFA or a mixture of several were used. Some organisms may be intolerant to the VFA and would be selected against, while others can grow in the presence of VFA. These isolations were conducted at pH 7 or pH 5 with or without 3% mixed VFA. Isolates were also obtained at pH 4, and higher or lower pH could also be used. Some organisms could be isolated at higher VFA mixtures, such as 6% total VFA or 10% VFA. The lower pH and the aerobic conditions selected for organisms that produced greater molar ratios of ethanol to acetic acid even when incubated at pH 7 under similar conditions following the isolation.

TABLE 2

Exemplary Enrichment and Isolation Conditions to Obtain Microorganisms that Synthesize Alcohols to High Concentrations.

| | Enrichment | | Isolation | |
|---|---|---|---|---|
| No. | Alcohol | Gas Mix | Alcohol | Gas Mix |
| 1 | 6% Ethanol | $N_2$, air, $H_2$, or $CO_2$ | 0 | 3:1 $H_2:CO_2$ or 2:1 $H_2:CO$ |
| 2 | 10% Ethanol | $N_2$, air, $H_2$, or $CO_2$ | 0 | 3:1 $H_2:CO_2$ or 2:1 $H_2:CO$ |
| 3 | 4% 1-Butanol | $N_2$, air, $H_2$, or $CO_2$ | 0 | 3:1 $H_2:CO_2$ or 2:1 $H_2:CO$ |
| 4 | 6% 1-Butanol | $N_2$, air, $H_2$, or $CO_2$ | 0 | 3:1 $H_2:CO_2$ or 2:1 $H_2:CO$ |
| 5 | 3% 1-Propanol | $N_2$, air, $H_2$, or $CO_2$ | 0 | 3:1 $H_2:CO_2$ or 2:1 $H_2:CO$ |
| 6 | 6% 1-Propanol | $N_2$, air, $H_2$, or $CO_2$ | 0 | 3:1 $H_2:CO_2$ or 2:1 $H_2:CO$ |
| 7 | 0 | 3:1 $H_2:CO_2$ | 0 | 3:1 $H_2:CO_2$ |
| 8 | 0 | 2:1 $H_2:CO$ | 0 | 2:1 $H_2:CO$ |

Medium for enrichment, isolation, screening and initial experiments was as described for in vitro digestion according to the manual by H. K. Goering and P. J. Van Soest, 1970. (Agricultural Handbook No. 379 entitled Forage Fiber Analyses (Apparatus, Reagents, Procedures, and Some Applications, Agricultural Research Service of the United States Department of Agriculture), which is incorporated by reference, except carbonate and bicarbonate salts (e.g. $NaHCO_3$, $NH_4HCO_3$) were replaced with equi-molar phosphate buffer salts (e.g. $NaH_2PO_4$, $NH_4H_2PO_4$) adjusted to pH 7 or pH 5 unless otherwise indicated. Macro minerals (e.g. calcium, magnesium), microminerals (e.g. iron), tryptic digest of casein, ammonia, sulfide and cysteine reducing agents, and resazurin were used as described by Goering and Van Soest (as cited). Media were boiled under 1 atm $N_2$ gas. The same media formulae were used for initial enrichment, agar roll tubes, broths, slant tubes, and agar plates. However, roll tubes, slant tubes and agar plates also contained 2% agar (BactoAgar). Media used for pure cultures (everything but the initial enrichment) were combined with 20% autoclaved rumen fluid to provide potential unknown growth factors. For some enrichments and isolations, some nutrients were omitted to select for organisms that do not require these nutrients or can synthesize their own. For example, ammonia may be omitted and amino acids used instead, or the other way around to select for organisms that synthesize protein from ammonia or degrade protein and use amino acids.

Enrichment. Media usually minimized extraneous sources of energy (e.g. glucose), to select for organisms that could grow from the energy they captured from the gases or from the alcohol added. Medium (45 ml) was transferred to each flask. Rumen fluid was collected from the cow's rumen through a fistula and was initially prepared by blending for 1 minute and straining though cheese cloth followed by glass wool. Carbon dioxide, run through a copper column to remove $O_2$, was perfused over rumen contents and into containers to maintain anaerobic conditions. Rumen inocula (5 ml) was added to each 250-ml flask. Large flasks relative to the volume of liquid were used so the headspace composition of gases did not readily change. Flasks were sealed with butyl rubber stoppers, and if needed vacuum was applied to remove initial head space gas before perfusion with corresponding treatment gases using a needle and syringe. Cultures were incubated in a shaking water bath for 3 days, and new gases were perfused at least daily. New flasks were prepared with 45 ml of media, and 5 ml of subculture was added from the previous fermentation. These flasks were again incubated for 3 days, and again sub-sampled. Each enrichment process included several cycles of sub-culturing and growth. Many variations on enrichment culture conditions are acceptable or advantageous, and can be applied.

For each enrichment and roll tube, the temperature of incubation was 39° C. unless indicated otherwise. Organisms were also selected at 55° C. and other temperatures could have been used. Using different temperatures selects for organisms that thrive at different temperatures. Initially, various concentrations of alcohols were used. These conditions selected for organisms that could utilize the alcohols, and which therefore also had the enzymes to make the alcohols. The same can be done for specific carboxylic acids. Each enrichment and isolation was attempted with media buffered to pH 7, pH 5, or pH 4. The lower pH favored alcohol producers and the isolates that resulted produced a greater concentration of ethanol and other alcohols relative to acetic acids and other volatile fatty acid production.

Isolation. Roll tubes and agar plates used the same medium as for enrichment but also contained 20% strained and autoclaved rumen fluid for micronutrients. The prepared medium (9 ml) was transferred to sterile test tubes while still hot from boiling Tubes were cooled to 55° C., and inoculated. Subcultures from the last enrichment were diluted serially in media to obtain cultures from 1 to $10^{-14}$ viable cells per 0.5-ml inocula. Roll tubes were prepared for each level of dilution, but concentrating on the 10' to 10' dilutions. Once inoculated, tubes were perfused with gas, stoppered, and rolled on ice to make the gel harden. Tubes were incubated for 24 to 48 h at 39° C. and independent colonies selected from these. Only organisms that could grow using the gases as an energy source were selected in the roll tubes, in the present case, and pH indicators in the roll tube agar were used to identify acid-producing and non-acid-producing isolates. In later isolations, agar plates were incubated in 32-liter pressure cookers under the desired gas pressures. These anaerobic chambers were easier to manipulate en masse than individual tubes. Some plates were buffered to pH 4, 5 or 7 and sometimes VFA were included.

Maintenance. Colonies were selected from among the colonies in roll tubes and agar plates, and were transferred to broth for short-term maintenance. The broth was of the same composition as media for other purposes, but did not contain agar. All cultures were maintained in large tubes leaving a high proportion of headspace, the ratio of $CO_2$ to $H_2$ or CO to $H_2$ that favors synthesis of the alcohols, and gas pressures of 2 atm to 4 atm. Broth cultures were maintained at 39° C. until they become cloudy, and new gas mixes were perfused if necessary. Broth cultures (5% final concentration, vol/vol) were transferred to new media one to two times per week. After two to three cultures, 0.1 ml culture was transferred to a slant culture in a 25-ml tube with 10 ml media on a slant to increase surface area). The inocula were added on top of the agar, which was maintained under $CO_2$ and $H_2$ or CO and $H_2$ in the thermodynamically favored ratio. These were initially incubated at 39° C. until colonies formed (16 h), and then stored at 25° C. or 4° C. for up to a month. Cloudy broth cultures were also stored by adding 15% glycerol (final volume) and freezing in liquid nitrogen; once frozen, these colonies were stored at -80° C.

Screening. Screening of microorganisms addresses whether they can synthesize a certain alcohol or acid from $CO_2$, CO, and $H_2$, and the extent to which they are tolerant to the product. The isolates derived as described were screened by transferring 0.5 ml broth to 9.5 ml media (as described, no agar). Tubes were perfused with mixtures of $CO_2$, CO and $H_2$ to favor synthesis (e.g. 3:1 ratio of $H_2$:$CO_2$) of the desired product preferably under at least 2 atm total gas pressure. Preferably 4 atm total gas pressures are used. However, successful isolations were also performed with only 1 atm total gas pressure with the ideal ratio of gases. The pH of the media was adjusted to 7, 5, or 4 and 3% or 6% mixed VFA added for different runs. Samples were also incubated with and without initially including 6% or other concentration of an alkyl alcohol in the media. The cell growth was determined by turbidity, and alcohols and acids were measured by gas chromatograph at time=0, and other time points (e.g. 3 d and 5 d). All colonies were typically screened after first isolating them by adding the colony directly to a test tube with media, incubating with $H_2$ and $CO_2$ and determining which isolates produce the highest concentrations of desired products or show other desired traits. The isolates that appeared to be most ideal were subcultured and incubated again in fresh media in replicate to verify results and test for effect of different conditions (e.g. pH, gas pressure) of the fermentation.

Improving Organisms That Synthesize Alcohols or Acids

These same conditions to enrich or isolate microorganisms that produce high concentrations of alkyl alcohols or acids from $CO_2$, CO and $H_2$ were used to improve the isolated microorganisms. Some improvements occur in the enrichment or isolation process although the improvements may not be observed. Pure cultures of microorganisms can be incubated with the ratio and pressure of gases that thermodynamically favors synthesis of the desired alcohol or acid, under pressures (e.g. 2 to 4 atm or higher), and in the presence of the products to which tolerance is desired. Under these conditions, organisms that produce the most of the desired product thrive, while those that produce more of the undesired product waste energy and become diluted. Over many generations, which can occur in a matter of days, organisms evolve under these conditions that can synthesize greater quantities of the desired product relative to other products, at faster rates, and that are more tolerant of the product and potential co-products. Mutation rate can be increased by brief exposure to UV light or other mutagen combined with thermodynamic controls. Using these conditions and several subcultures for enrichment of pure cultures, organisms can be developed that make only the desired products, at high rates, with high tolerance to those products. This process of directing evolution (or non-specific mutagenesis) selects for organisms on the basis of the products they make, and selects for organisms that can tolerate very high concentrations of products.

Previous attempts at non-specific mutagenesis did not select for organisms that produced specific products, so one could not increase the amount of those products produced as a portion of total products. As a result, many different products were made. In addition, previous methods at adaptation to higher levels of products (e.g. alcohols) by growing the isolates with the products selected against further production of those products (because they became thermodynamically limited). By maintaining highly thermodynamic ally favorable conditions for the production of desired products (e.g. alcohols) organisms are adapted that produce the desired products even at high concentrations. Using this process, the inventors contemplate isolating organisms that can produce a desired alcohol or desired carboxylic acid nearly exclusively, and at very high concentration. For example, some natural organisms already isolated produced virtually nothing but ethanol at greater than 10% ethanol concentration by volume, but with use of the methods of mutagenesis (or directed evolution) described in this application, the ethanol concentration could approach 20% or more. Organisms could be adapted to produce virtually nothing but the desired alcohol at any concentration between 0 to 20% lower alkyl alcohol by volume.

SPECIFIC EXAMPLES

Example

Enrichment and Isolation of Microbes that Produce Carboxylic Acids and Alcohols

In one example experiment, organisms were isolated by the procedures described in this application. The pH for enrichment and isolation was 7. The incubation temperature was 39° C. Twelve enrichment treatments were used in a 6×2 factorial arrangement, with inclusion of one of 6 alcohols with $N_2$ or air. Media for the enrichment contained one of the following alcohols: 6 or 10% ethanol, 4 or 6% 1-propanol, or 4 or 6% 1-butanol. The gas phase during enrichment was $N_2$ or air at 1 atmosphere. After enrichment, agar for isolation did not contain alcohols (removed substrate) but headspace gas was 3:1 $H_2$ to $CO_2$ at 1 atm in roll tubes.

Microorganisms grew in all enrichment treatments, and isolates were obtained from all treatments except for 6% 1-butanol. A total of 127 organisms were isolated based on their ability to grow on agar with $H_2$ and $CO_2$, and each isolate was screened by transferring the colonies to broth (as described) and incubating for 5 days under 1 atm gas pressure of 3:1 $H_2$ to $CO_2$ without shaking (although higher pressure and shaking may be preferred). Each isolate was incubated in a sealed tube with 5 ml of media and 10 ml of headspace gas.

Most of the isolates did not grow on synthesis gases or did not produce significant amounts of alcohol or VFA in broth after isolating the colonies. Using only 1 atm pressure may not have strongly favored microbes that grow on synthesis gas over those using residual energy in the media. However, several isolates did grow as indicated by increased turbidity, production of VFA or ethanol, and a decrease in headspace gas pressure. The 16 colonies that produced the most interesting profile of products (as measured by gas chromatography) were sub-sampled and again incubated in duplicate under similar conditions.

The concentrations of VFA and alcohols were measured after 5 days and 10 days. However, after 5 days about half of the headspace gas was incorporated into VFA or alcohols and growth did not continue. In addition, duplicate samples of each isolate were incubated with $N_2$ gas in the headspace instead of $H_2$ and $CO_2$ and under otherwise identical conditions, but cells did not grow or did not grow as much in those cases and did not produce as much VFA or ethanol. This negative control confirms that the organisms were growing from the $H_2$ and $CO_2$ gas and the energy from making VFA and alcohols. Example VFA profiles for organisms that produced VFA from synthesis gases are shown in Table 3. The results are for the mean of the duplicate samples from separate fermentations of the same isolate, which produced similar amounts of each product.

TABLE 3

Product profile of selected isolated isolates of microortanisms.

| Isolate | Acetate | Propionate | Butyrate | Iso-Butyrate | Valerate | Iso-Valerate | Ethanol |
|---|---|---|---|---|---|---|---|
| | | | Molar % of Total VFA | | | | |
| S3 | 56 | 10 | 34 | 0 | 1 | 0 | 3 |
| S13 | 36 | 6 | 48 | 2 | 2 | 6 | 1 |
| S90 | 95 | 2 | 0 | 0 | 2 | 1 | 3 |
| S99 | 46 | 4 | 2 | 18 | 4 | 27 | 7 |
| S120 | 42 | 2 | 1 | 20 | 1 | 34 | 20 |
| S121 | 45 | 5 | 4 | 18 | 1 | 27 | 15 |

Mean standard error = 0.07%, n = 30. Molar percentage means the molar ratio as a percentage of total VFA times 100. Molar ratio means the concentration of the individual VFA or ethanol produced divided by the concentration of total VFA measured.

Isolates S3 and S 13 were isolated after enrichment in 6% ethanol. Isolates S90 and S99 were isolated after enrichment in 4% propanol, and isolates S120 and S121 were isolated after enrichment in 4% butanol.

The results indicate a tremendous variation in which products the organisms could produce when incubated under similar conditions. Isolate S90 produced mostly acetate and small amounts of ethanol. Isolates S3 and S13 produced a high percentage of butyrate, and strains S99, S120, and S121 produced large amounts of iso-butyrate and iso-valerate. One isolate produced about 12% molar percentage as valerate but the duplicate did not grow so results are not shown.

Although some isolates only produced a small amount of alcohols, isolates S120 and S121 produced important concentrations of ethanol when incubated under the same conditions as other products. These isolates also produced 1-propanol, iso-propanol and 1-butanol. Profiles of alcohols were similar for both isolates, which produced 11.4 or 11.0 molar % as much 1-propanol as total VFA, and 3.3 or 2.8 molar % as much iso-propanol, and 2.9 or 2.8 molar % as much 1-butanol as total VFA for stains S120 or S121 respectively.

Wherein others have isolated organisms that could synthesize acetate or trace quantities of ethanol, the present results show that using the isolation techniques described in this application, organisms could be isolated that preferentially produced alcohols, including 1-propanol, and VFA that are seldom observed from synthesis gases, such as propionate, butyrate, iso-valerate, and iso-butyrate.

Animal nutritionists believed previously that branched chain VFA (iso-butyrate and iso-valerate) in the rumen were derived exclusively from amino acids in the feed, and adding them to the rations of ruminants increases animal growth and milk production, particularly for low-protein diets. The quantity of these VFA produced from synthesis gas by some of these isolates were orders of magnitude higher than the quantity of branched-chain amino acids in the media, and they were not produced in corresponding tubes with $N_2$ in the headspace instead of $H_2$ and $CO_2$. Thus, these VFA were produced by a previously-unknown process. These particular VFA are valuable as feeds for animals, including ruminants. The organisms themselves may be used to enhance digestion and metabolism in the gut.

Example

Effect of Enrichment pH

In one set of isolations, the effect of pH and inclusion of VFA in the media was tested for the enrichment phase otherwise as described previously. Enrichment treatments were compared in a factorial design with 2 pH levels (5 or 7), inclusion of VFA (1% of each: acetate, propionate, and butyrate) or not, for media with one of the alcohols (6% ethanol, 4% 1-butanol, or 4% 1-propanol), using $N_2$ or open air as the gas phase. Rumen fluid was used as the inocula which was incubated at 39° C. After enrichment and sub-culturing 3 times as described, cultures were isolated as described by incubating various dilutions on agar plates incubated in an anaerobic chamber with 2 atmospheres of gas with 3:1 ratio of $H_2$ to $CO_2$. Cultures grew under each enrichment condition, and isolates were obtained that grew on the synthesis gases for each enrichment treatment except no isolates were obtained from the enrichment in butanol under aerobic conditions (isolates were obtained from enrichment in 1-butanol under $N_2$).

Isolates were screened by incubating in broth at pH 7 under 2 atm pressure of 3:1 of $H_2$ to $CO_2$. Most produced low quantities of ethanol or alcohols, but several produced more than 20% as much ethanol as total VFA. Most of the isolates from this run grew on synthesis gases, but the main difference for the pH 7 treatment without added VFA compared to the last enrichment was the use of 2 atm pressure for both enrichment and screening. The higher pressures would greatly favor synthesis gas users during isolation and enable more of them to obtain energy from synthesis gas during screening. The pressure would also favor alcohols and longer-chain VFA.

The product profiles from some isolates are shown in Table 4. A total of 25 organisms (of 300 isolated in this run) produced a molar ratio of ethanol to acetate greater than 0.4. This means the concentration of produced ethanol in moles per liter divided by the concentration of produced acetate in moles per liter was greater than 0.4. One isolate (S241) produced a molar ratio of ethanol to acetate of 0.89, and one (S202) produced a ratio of 0.70. The molar ratio of ethanol to all VFA was 0.43 and 0.37 (mol/mol) respectively. These two isolates also produced other alcohols with the predominant alcohol after ethanol being 1-butanol. The isolates S241 and S202 also produced butyrate and propionate.

The low-pH enrichment in the present experiment provided a higher percentage of organisms producing alcohols and higher ratios of alcohols to other products. At low pH, the thermodynamics disfavors acid production and it also selects for alcohol producers. In addition, organisms that were enriched in air produced more alcohol when screened than organisms enriched under $N_2$.

TABLE 4

Product Profiles from Example Isolated Isolates.

| Isolate | Enrichment | Acetate | Propionate | Butyrate | Ethanol |
|---------|-----------|---------|------------|----------|---------|
|         |           |         | molar percentage | | |
| S241 | Media with VFA and 6% ethanol, pH 5 in $N_2$ | 48.0 | 8.9 | 39.1 | 43.0 |
| S202 | Media with 6% ethanol, pH 5, in $N_2$ | 53.4 | 10.5 | 31.5 | 37.3 |
| S392 | Media with VFA and ethanol, pH 7 in air | 48.2 | 40.1 | 8.0 | 7.3 |
| S247 | Media with VFA and 6% ethanol, pH 7 in $N_2$ | 34.3 | 14.0 | 49.4 | 9.7 |

Molar percentage as a fraction of all measured VFA (acetate, propionate, butyrate, iso-butyrate, valerate, iso-valerate).
Molar percentage = molar ratio times 100.

Microbial Characterization and Identification

All 32 isolates from the above isolation process were compared morphologically for differences. All isolates formed visible colonies on agar from synthesis gas within 5 days, and on glucose agar within 1 day. Colonies on agar were round, and yellow or white in color. All but one of the 32 isolates grew on glucose media in open air. Most of the isolates tested positive for gram stain, and were spherical cocci without spores present. Some isolates presented mostly as individuals, some were found in doublets, and other isolates were found in chains. Most of these isolates were negative to catalase test or slightly positive. One isolate was strongly catalase positive. The one organism that did not grow in open air, did grow on glucose media under strict anaerobic conditions. It was a spiral-shaped, gram-negative organism. Based on these characteristics, organisms appeared to be from several different isolates, especially from the genus *Enterococcus* and/or *Streptococcus* among others.

One of the best producers of ethanol and butyrate (S241) was further identified. Gene sequencing of 500 base pairs (bp)

in a region of 16S rRNA identified this organism as having 99.89% homology (1 bp differed) with *Enterococcus avium*. Greater than 97% homology was also observed with *E. gilvus* (99.84), *E. malodoratus* (98.63), *E. pseudoavium* (98.21), and *E. Raffinosus* (97.89). Although the organism may not be of the same species as any of these, less than 97% homology is generally used to denote a different species. In other words, based on the genetic sequence alone, one cannot rule out that the organism is a member of one of the species listed. However, the ability to produce high concentrations of ethanol or butyrate from synthesis gases was not known for any member of the genus *Enterococcus*, or for any other facultative anaerobe.

The diversity of the organisms that were isolated shows that it is possible to isolate many different species of organism using the techniques described, and many different species harbor the traits making it possible for them to produce alcohols or carboxylic acids from synthesis gases. Many of the isolates would be robust and easily maintained and used in a scaled-up procedure. They grew quickly and could be maintained or grown on glucose or synthesis gases, and were aerotolerant.

Example Comparison of CO and $CO_2$

All 32 stains from the preceding experiment were also incubated with a 2:1 ratio of $H_2$ to CO compared to a 3:1 ratio of $H_2$ to $CO_2$. Other conditions were similar to previous incubations including 2 atm total pressure, initial pH of 7, temperature of 39° C. Each isolate was incubated in duplicate fermentation tubes for each set of gas. Concentrations and profiles of products were similar across most isolates. One isolate produced more acetate and less propionate and butyrate with CO compared to $CO_2$. Two isolates did the opposite and produced more acetate and butyrate but less propionate with CO compared with $CO_2$. The results indicate the approach can be used for both CO and $CO_2$ with equal effect for most isolates.

Example of Controlling Production of VFA and Ethanol in Fermentation

Altering the conditions of the fermentation for producing alcohols (e.g. lower pH, accumulation of VFA) could further increase the molar ratio of ethanol to VFA produced. Four isolates were incubated in a factorial arrangement with different pH (4, 5, 7) with or without added VFA (2% of acetate, propionate and butyrate). Each treatment was also tested with three levels of ethanol at the start (0, 6%, 10% by volume). The added acids and lowest pH inhibited the production of all products and decreased microbial growth. These organisms were not well adapted to the high VFA concentrations but others could be isolated that are better suited to high VFA concentrations by using more VFA in the enrichment media. However, at neutral pH without added VFA, addition of ethanol resulted in much higher ethanol production (2 to 4 fold increase) and nearly complete inhibition (>90%) of VFA production for 3 of the four isolates tested.

One strategy for ethanol production is to use organisms that tolerate carboxylic acids and alcohols and use these organisms to produce both alcohols and carboxylic acids. Another strategy is to use organisms and conditions that do not produce carboxylic acids to produce only alcohols. Of course, other organisms could be used to produce only carboxylic acids. The methods described in this application can provide organisms and conditions for all three strategies.

Previously, addition of ethanol was shown to inhibit VFA production and to increase ethanol production from cellobiose for several rumen microorganisms incubated under conditions to thermodynamically favor ethanol production. In addition, ethanol addition was shown to shift mixed-culture microorganisms in rumen fluid toward ethanol production when incubated under $H_2$ pressure. Thus, it appears that many microorganisms are tolerant to ethanol in the media, and in fact can grow in the presence of ethanol if other products including gases are controlled to make it thermodynamically feasible to produce additional ethanol. In fact, ethanol appears to inhibit VFA production and the high concentrations of ethanol therefore shifts fermentation toward greater ethanol production.

If the concentrations of gases and other metabolites are not controlled, the higher ethanol concentrations in the media would thermodynamically limit additional ethanol production, and together with the inhibition of VFA production, the organisms would not be able to obtain energy and grow. Thus, the apparent ethanol intolerance that has been faced by previous investigators can be overcome by controlling the thermodynamic conditions, especially gas composition and pressures. Controlling the fermentation to maintain some amount of ethanol in the fermentation can virtually prevent VFA from being produced at all, and therefore would favor further ethanol production, even beyond 10% ethanol by volume of media as was observed in the current study. Further development of organisms by growing them in media with ethanol would also select for ethanol producers and result in degradation of the ability to produce acetate.

Process to Produce Alcohols or Carboxylic Acids

One or more species of isolated microorganism or mixed cultures taken from a microbial environment are used in a large-scale process to produce alkyl alcohol or carboxylic acids from synthesis gases. In this process, certain steps are used to result in optimal ethanol or other alcohol production.

1. Optimal conditioning of the media to insure anaerobic conditions for production.
2. Addition of microorganisms that can assimilate gases for synthesis of the desired product (e.g. alkyl alcohols or acids).
3. Maintenance of the optimal temperature for the conversion to take place.
4. Addition of gases to maintain the ratio of synthesis gases that is calculated to be thermodynamically optimal for the desired product.
5. Maintenance of gas pressures to favor desired products from the gases.
6. Using various means to increase the rate of solubilization of gases including: mixing, aerating, agitating, vibrating, increasing surface area, other means or a combination of these means.
7. Removing alkyl alcohols, carboxylic acid, and other products from the fermenter
8. Separating or further treating removed liquids and solids.

The industrial process to produce lower alkyl alcohols or volatile fatty acids uses microorganisms to convert $CO_2$, CO and $H_2$ to desired products. These organisms may be aerobic, anaerobic, facultative anaerobic, or strictly anaerobic. Most alcohols or organic acids are produced under anaerobic conditions in any case. The microbial cultures that are used can be mono-cultures or mixed cultures of microorganisms that are selected to predominantly produce a desired product, and which are tolerant to that product.

It may be advantageous to use a pure culture of organisms to prevent production of undesired products. The pure culture would have a reduced ability to produce the undesired products. If using a pure culture, sterile conditions could be used to prevent contamination. Alternatively, some level of contamination may be acceptable if the reactor conditions favor the desired organisms and desired products. The cultures that can be derived using the methods in this application are ideal for this process because these organisms are robust, grow quickly, and produce desired products at a high concentration. These cultures would readily scale to a large-scale fermentation.

Undefined mixed cultures could also be used and doing so could obviate the need for sterile conditions. The decision on whether to use a pure culture and sterile conditions depends on the products desired, the extent to which a certain number of specific products is desired, and the degree to which the conditions favoring a certain product need to be maintained. For example, with very restrictive conditions (pressures, ratios of gases, pH), certain products can be favored even without using pure cultures. However, it may be more cost effective to use pure cultures and less restrictive conditions. Alternatively, the mixed culture and unrestrictive conditions could provide a mixture of products that could be separated and used, and the potentially greater cost of separation could be balanced by the lower cost and higher efficiency of the fermentation. The best option depends on the market conditions.

Various sources of gases can be used depending on availability and price. Gases can be derived from heating biomass, fossil fuel (e.g. coal), or other organic product (e.g. plastic) through a process of gasification. The gases can also be derived from the waste stream of an industrial or agricultural process. For example, residual gases from hydrocracking of fossil fuel can be used. Gases can be obtained from anaerobic digestion with a mixed culture or a pure culture that produces $H_2$ and $CO_2$. Hydrogen can be produced from sunlight using algae or plants, or from electrolysis. Carbon dioxide can be obtained from combustion or other oxidation process. Steam distillation of methane also produces gases. For this process, the ($CO_2$ and $H_2$) gases do not need to be separated, which would reduce cost. If the gases only contain low concentrations of $CO_2$ or $H_2$, greater total pressures can be used to develop conditions to make it feasible to synthesize organic compounds. Different sources of gases can be mixed to provide more optimal ratios of gases. In addition, sources of gases that may contain potential contaminants (e.g. sulfide) are also acceptable. The mixed gases may be filtered through a 0.2-micron filter to remove potential microbial contaminants before feeding the reactors containing the developed microorganisms.

In some cases the process may be improved by pressurizing the system to a few atmospheres or more, or by mixing different sources of gases to obtain a desirable ratio, however once the organisms are selected and developed, the exact composition of gases is not as critical. For some microbial cultures and for some desired products greater attention to pressure and composition of gases is necessary. For example, undefined cultures would require more precise manipulation of the gas composition than pure cultures. Production of alcohol or longer-chain carboxylic acids would require more precise conditions than acetate production.

The composition and pressure of the gases needed would be determined using a thermodynamic model that was described as an aspect of this application. The composition and pressure needed to make production of a desired product thermodynamically feasible at a desired concentration is calculated. Furthermore, the conditions needed to restrict production of undesired products would also be determined based on the thermodynamics as described in this application.

Gas is bubbled into the reactors through a gas disperser on a rotating arm. Alternative methods of gas distribution are also acceptable. Gas can also be solubilized from the headspace by other forms of agitation such as vibration or vortexing. The same gas can be re-circulated from the headspace, and gas can be replaced as it is used to maintain the desired pressure.

The reactor vessel is heated to an optimal temperature for growth (e.g. 40° C.). Cooler temperatures (e.g. 25° C.) can be used to save energy cost but it may slow the fermentation rate. Warmer temperatures (e.g. 55° C.) can also be used to increase the rate of fermentation, and to contribute to decreasing the potential for contaminant organisms. The temperature used is suited to the isolate of organism that is used.

The fermentation pH may be regulated by computerized monitoring and adjustment by addition of buffers or bases. The pH may be maintained near 5 for alcohol production, but some stains grow faster at higher pH (although may make more acids), or lower pH may be used to more strongly inhibit acid production. Neutral pH favors solubility of $CO_2$ and bicarbonate ($HCO_3^-$). Generally, a pH between 4 and 7 has been used in bench-top experiments with organisms exhibiting abilities to make desired products in this range. However, organisms are known to produce alcohols at even lower pH such as pH 2, and a lower pH could be used.

An aqueous broth in the reactor contains simple nutrients (e.g. ammonia, minerals, cofactors). Some microbes can digest and use microbial protein while others synthesize protein from infused gases and ammonia. Both options are possible. Including an organism that digests other microbes at a controlled rate decreases the need to replace nutrients, but also may decrease the activity of organisms using the synthesis gases. On the other hand, if the proteolytic activity is minimized the accumulated microbial protein can be removed periodically and the nutrients replaced. The microbial protein can be separated and used as a high-value animal feed. The protein can be separated by centrifugation, or attachment to another feed product like hay or plant fiber, or by flocculation with an addend.

The organisms that are used for this process tolerate high concentrations of the desired alcohol or acids or both. The acids are typically removed by adding a divalent cation such as calcium ions or magnesium ions, which form a salt with the volatile fatty acids. The alcohols are commonly removed by distillation. When an organism produces both alcohol and one or more VFA, the products may be separated by both methods. If the organisms begin to show signs of stress due to the over accumulation of a product, that product may be removed while other products continues to accumulate. The carboxylic acids can be precipitated even before the fermentation is complete if too much acid accumulates. If the remaining cation concentration is too high after precipitating the VFA, excess cation can be removed by adding carbonates, which also precipitate with divalent cations. Media can then be recycled.

Maintaining microorganisms in the fermenter while removing waste and products may be desirable. One way to maintain microorganisms in the digester is to distill ethanol intermittently using vacuum pressure distillation, or gas stripping during the fermentation. Alternatively, microbes can be separated from removed liquids with centrifugation or filtering and returned to the fermenter. However, it may not be necessary to recycle the microorganisms. Liquids can simply be removed and alcohols distilled out, and the liquids recycled to the fermenter.

Processes already being developed using microorganisms to convert $CO_2$ and $H_2$ or CO and $H_2$ to acetate, ethanol or other alcohols or carboxylic acids can be adapted using the innovations described in this application. For example, these procedures may be improved by increasing the pressure of the gases, manipulating the ratios of gases if warranted, and using novel organisms isolated using the process described in this application to produce much higher concentrations of alcohols or carboxylic acids than has been achieved before.

Example Process to Produce Alcohols from Synthesis Gases

For production of alcohols, the optimal ratio of $H_2:CO_2$ is higher (3:1) than for production of acetic acid (2:1). The production of alcohols is also more sensitive to the ratio of $H_2:CO_2$ and total pressure than production of acetic acid. The media pH may be lower than for VFA production to favor alcohols over VFA. A pH from 4 to 5, or even less than 4 may be used, but a higher pH may also be used to increase the rate of production.

Some co-products may be produced, especially VFA when alcohols are desired, especially if using an undefined culture. These co-products can be converted to other products or fuels or removed for a subsequent process. These products might be catalyzed to ethanol, other alcohols, or alkanes (methane, ethane, propane, butane) using a separate process, which may be a separate fermentation process or a chemical method. Alternatively, the VFA can be converted to $H_2$ and $CO_2$ or $CH_4$, which may be synthesized to alcohols or used separately. The VFA can also be converted to alkyl alcohols using low-pH conditions and gas concentrations that simultaneously favor alcohol degradation and synthesis of alcohols.

One unique aspect of this approach is the organisms produce high concentrations of ethanol, such as greater than 6%, and preferably greater than 8% or even more preferably greater than 10% ethanol by volume. With further improvement of organisms using the process described in this invention, as much as 20% alcohol may be produced. Another aspect is the possibility of producing longer chain alcohols like propanol and butanol.

Adjusting the gases to a ratio of $H_2$ to $CO_2$ of 3:1 increases the thermodynamically feasible concentration of ethanol that can be produced from the gases, and increases the concentration of ethanol that is obtained. Another way to increase the thermodynamically feasible concentration of alcohol produced is to increase the pressure above atmospheric pressure. For example, even if very low concentrations of $H_2$ and $CO_2$ result from the waste stream of a process, these low concentrations can be captured by providing some additional gas ($CO_2$ or $H_2$) to provide a ratio of $H_2$ to $CO_2$ that is readily used for alcohol production (e.g. 3 to 1). In addition the total pressure can be increased, which increases the partial pressures, and makes it feasible to produce greater concentrations of the alcohol.

Example of Producing Carboxylic Acids from Gases

Similar procedures to those used for alcohol production can be used to produce acids, such as VFA, rather than alcohols but the ratios of gases would be adjusted to mainly produce the desired acids. Because acids are a common product of mixed culture fermentations, if a mixture of gases is desired, aseptic conditions and defined microbial cultures would not be needed. The profile a gases can be controlled by adjusting the thermodynamics. Longer-chain carboxylic acids are favored by increasing total gas pressures, increasing the ratio of $H_2:CO_2$ or $H_2:CO$ and decreasing pH. However, defined cultures can be used to obtain a single or limited number of desired acids, such as acetic acid, propionic acid, or butyric acid. The acids can be used subsequently for alcohol production in a different process, which may be a chemical process rather than a fermentation process. For example, acetate may be converted to ethanol, propionate may be converted to a propanol, or butyrate or acetate may be converted to butanol. Any of these acids may be converted to alkanes, including longer chain alkanes, in a subsequent process. Or they may be used to construct bio-polymers or they may be separated and sold as chemicals. Free fatty acids can be precipitated with divalent cations (e.g. $Ca^{2+}$, $Mg^{2+}$) to form salts such as calcium acetate or magnesium butyrate. If VFA are produced as byproducts of alcohol production, both may be removed and used. For example, some organisms produce some acetate and ethanol and the acetate can be removed by adding CaOH and causing it to precipitate. If the concentration of calcium becomes too high, it too can be precipitated by adding bicarbonate to form calcium carbonate.

Example of Producing Animal Feeds from $CO_2$, CO and $H_2$

Mixed rumen microbes taken directly from the rumen of a cow were incubated in vitro while perfusing different mixtures of $CO_2$ and $H_2$, and the total microbial protein and VFA concentrations increased substantially compared to when gases were not perfused. Interestingly, the profile of VFA changed slightly, and all VFA measured increased (acetate, propionate, butyrate, valerate, iso-valerate, iso-butyrate). Cattle obtain much of their protein from the high-quality microbial protein synthesized in the rumen during degradation of substrate. They obtain most of their energy from the VFA produced by these microorganisms. This example shows that synthesis gases can be used to produce microbial protein and VFA, both of which can be used for animal feeds. The microbial protein could be used for cattle or most other animals. Many processes produce one or more of the synthesis gases that can be converted to other products including animal feeds. Interestingly, in this example pure cultures were not needed. Undefined mixed cultures produce many products but they don't need to be sterile or aseptic and they do not have requirements for as many micronutrients like vitamins because some of the microorganisms can produce these vitamins.

An undefined mixed culture or a pure culture of microorganisms would be provided with needed micronutrients for growth including minerals and vitamins, and buffers or the regulated addition of bases would be used to maintain neutral pH. A source of nitrogen and sulfur would be included. The fermenter may need a source of amino acids or protein in some cases, or it may need ammonia or urea in other cases, depending on the microbial culture. Gases will be perfused into the culture possibly using a bubble disperser or other method to increase solubility, pressures may be applied, gases may be re-circulated, and ratios of gases may be adjusted to increase the rate of production or to select for desired products. The products can be fed to animals directly, or after drying or mixing with other feed, or they may be separated and used for separate processes or types of animals. Even when the VFA or alcohols are used in one process, the microbial protein can be fed to animals.

Thermodynamics for Synthesis of Alcohols or Acids from $CO_2$, CO and $H_2$.

The process used as an aspect of this invention advances thermodynamic analysis in many ways. Firstly, multiple thermodynamic equations were solved simultaneously to enable prediction of which pathway branches are available, and to integrate the effects of each reaction on each other. Secondly, thermodynamics was applied to the fitness of organisms that carry out a given reaction relative to other organisms. If the $\Delta G$ for $CO_2$ and $H_2$ to acetate is much more negative than for $CO_2$ and $H_2$ to ethanol for a certain set of concentrations and pressures, organisms that make acetate will grow faster than those that make ethanol. To encourage ethanol production within an organism, or to encourage organisms that make ethanol to out compete with acetic acid producers, the metabolite concentrations must be manipulated to favor ethanol producers and production of ethanol. Under these conditions, ethanol producers can be used, enriched, selected, mutated and manipulated. The same procedure is used for any desired product and will also be demonstrated for other alcohols and for different carboxylic acids.

Conditions That Affect the $\Delta G$ for Synthesis Reactions

In a natural microbial ecosystem, there are many different reactions that can use $H_2$ and $CO_2$ to produce organic compounds when the concentrations of $H_2$ and $CO_2$ are high enough. When the concentrations of the gases are low, the organic compounds are degraded to $H_2$ and $CO_2$ instead. Which direction the pathways flow depends on the change in free energy of the reaction. Microorganisms can only grow if they capture some of the benefit of the free energy change ($\Delta G$). For example, typically about 44 kJ of energy in $\Delta G$ is used to convert a mole of ADP to ATP.

The $\Delta G$ for different concentrations of reactants and products and temperatures can be calculated as described previously ($\Delta G=\Delta G°+\ln \{[products]/[reactants]\}$). Where this value is a negative number, the reaction can proceed spontaneously in the forward direction. Where it is a positive number, the reaction cannot proceed without the input of energy or it may proceed in the reverse direction. The magnitude of the absolute value of the $\Delta G$ indicates how much energy may be paired with the reaction. For example, a $\Delta G$ less than (more negative than)-44 kJ indicates the potential for production of one mole of ATP.

The calculated $\Delta G$ values for three reactions important to fermentation and synthesis from gases are shown in FIG. 1. In this example, a constant total pressure of 1 atm was maintained, but the ratio of $H_2$ to $CO_2$ increased. At the left end of the diagram, typical conditions in an anaerobic fermenter or the rumen of the cow are shown. Note that the $\Delta G$ for methane synthesis from $4H_2$ and 1 $CO_2$ is about −50 kJ/mol of methane produced. Therefore, it would be possible to produce about 1 ATP per mole of methane. The corresponding $\Delta G$ for acetate or ethanol synthesis from $H_2$ and $CO_2$ are positive. While the $\Delta G$ for acetate synthesis is near 0, that for ethanol synthesis is strongly positive (+75 kJ/mol). Under these conditions, ethanol can be converted to acetate or might be degraded to $CO_2$ and $H_2$. As the $H_2$ to $CO_2$ ratio increases, the $\Delta G$ for methane continues to decrease and then begins to slowly increase. The minimum value occurs at a ratio of 4:1 $H_2$ to $CO_2$ on a molar basis or volume basis. At the minimum, nearly 3 ATP could be generated per mol of methane rather than one. This explains why methanogens grow faster under these conditions. In addition, as the ratio of $H_2$ to $CO_2$ increases, it also becomes thermodynamically feasible to produce acetate from $CO_2$ and $H_2$. The minimum value occurs at a ratio of 2:1 $H_2$ to $CO_2$, and it is possible to produce more than one ATP per mole at this ratio. The $\Delta G$ for ethanol synthesis decreases as well until it reaches a minimum at a ratio of 3:1 $H_2$ to $CO_2$. Wherein the $\Delta G$ for ethanol synthesis initially decreases faster than for acetate synthesis, and the $\Delta G$ for both acetate and ethanol decline faster than for methane, the curves converge as the ratio increases toward the minimum. Thus, near the minimum, it becomes possible to make all of the products. After reaching the minimum $\Delta G$, the curves for acetate and ethanol increase faster than for methane, making it more favorable to produce methane than the other two as the $H_2$ to $CO_2$ ratio increases further.

This graph explains many decades of research results conducted with anaerobic systems. It is clear from this graph why methane is the favored product under typical fermentation conditions and why methane is especially favored at low or high ratio of $H_2$ to $CO_2$. If the fermentation is designed to degrade acetate to methane and $CO_2$, either a low or a high ratio of $H_2$ to $CO_2$ is required. Furthermore, acetate and ethanol are only produced when there is both $H_2$ and $CO_2$ present. If the pH is decreased, the curve for acetate would increase to approach that of ethanol. If the pressure is increased, all of the curves would decrease but the ethanol curve would decrease the most, the acetate curve would decrease the second most, and the methane curve would decrease the least. Thus, decreasing pH or increasing total gas pressures are ways to favor ethanol or both ethanol and acetate over methane.

Figure 2:
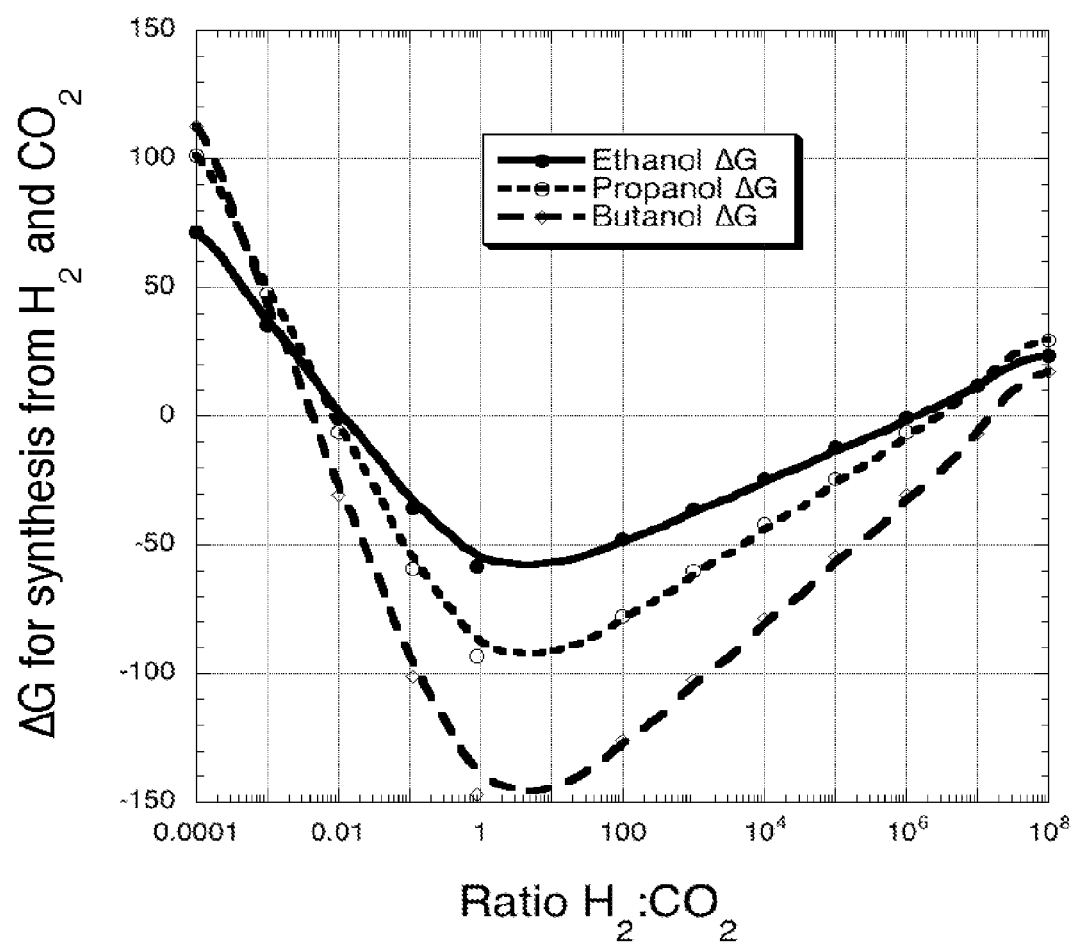
FIG. 2 indicates the change in free energy ($\Delta G$; kJ/mol) for synthesis of alkyl alcohols from $H_2$ and $CO_2$ as the molar ratio of $H_2$ to $CO_2$ increases. This figure shows that energy for forming alcohols is greatest for longer alcohols at the ratio for maximal synthesis (3:1 for $H_2$ to $CO_2$), but otherwise shorter alcohols are favored over longer alcohols. Model assumed 1 atm. total pressure, 0.001 M aqueous ethanol, 1-propanol and 1-butanol, temperature 40° C., pH=6.5.
Figure 3:
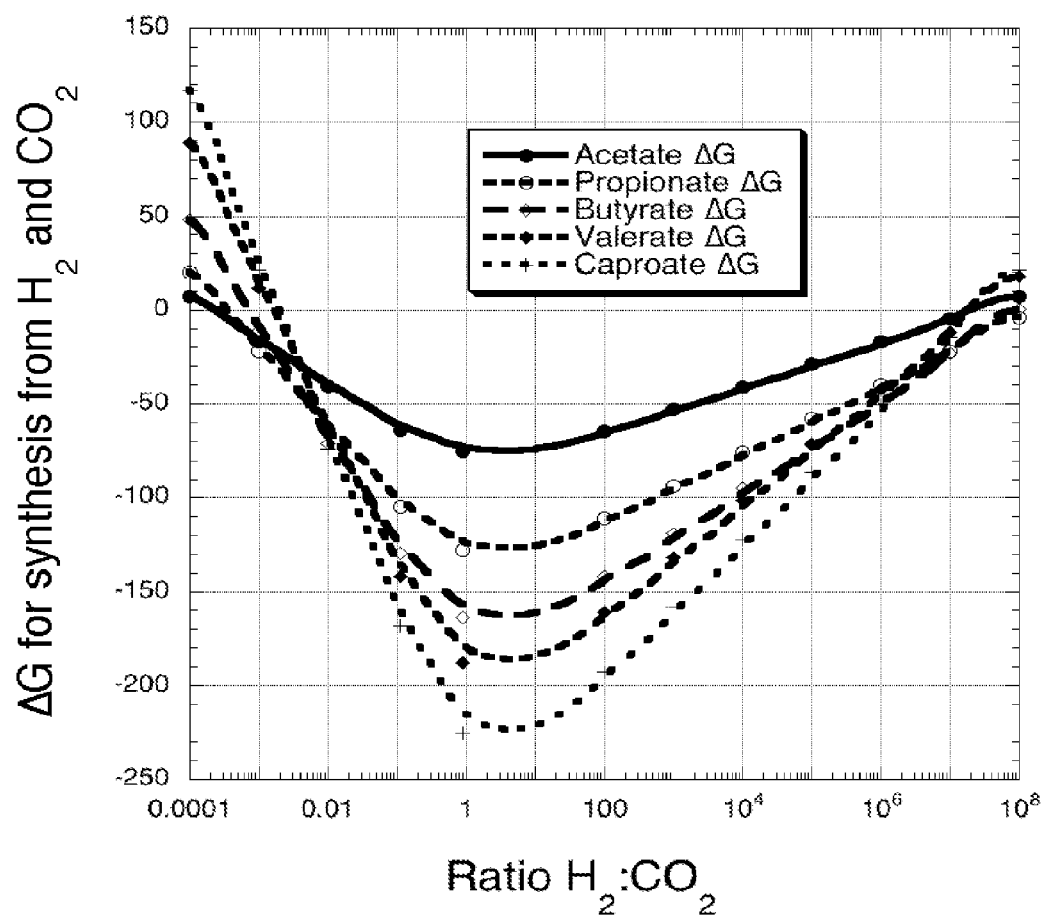
FIG. 3 indicates the change in free energy ($\Delta G$; kJ/mol) for synthesis of carboxylic acids ($C_2$ to $C_6$) from $H_2$ and $CO_2$ as the molar ratio of $H_2$ to $CO_2$ increases. This figure shows the increase in energy available to make longer carboxylic acids at the ratio for maximal synthesis (between 2:1 to 3:1 for $H_2$ to $CO_2$), but that shorter carboxylic acids are favored at both lower and higher ratios of $H_2$ to $CO_2$. Model assumed 1 atm total pressure, 0.001 M aqueous carboxylic acids, temperature 40° C., pH=6.5.

The $\Delta G$ for production of ethanol, propanol, and butanol are shown in FIG. 2. Initially, production of alcohol is not feasible under the conditions shown. As the $H_2$ to $CO_2$ ratio increases, first butanol, then propanol, and finally ethanol cross the line Y=0 representing thermodynamic feasibility. At $H_2$ to $CO_2$ ratio of 3:1, each $\Delta G$ is minimized with the longer alcohols more favored than the shorter ones. Thus, conditions of a ratio of 3:1 favor any alcohol production with enough energy left over for ATP production. The same conditions for carboxylic acid production are shown in FIG. 3. In this case, acetate is the first to become thermodynamically feasible, but as the $H_2$ to $CO_2$ ratio increases longer-chain carboxylic acids also become feasible, with the longer acids more favored than the shorter ones.

These data show how to establish conditions for synthesis of alcohols (including longer-chain alcohols) or longer-chain carboxylic acids from $H_2$ and $CO_2$. Wherein many different potential reaction pathways compete for the $H_2$ and $CO_2$ these conditions need to be understood to select for organisms to make certain products or to establish conditions in the digester to make it feasible, and even favorable, for the desired products. Note that by "feasible" we mean the $\Delta G$ is negative and it is possible to make the product. By "favorable" we mean the $\Delta G$ is negative for the desired product and $\Delta G$ may be positive (or at least less negative) for a major competing reaction. Thus, the desired product will be produced to a greater extent than other products.

Example Calculations from Thermodynamic Model

Although a model encoded with software provides much greater flexibility for exploring the potential to control a fermentation system, example calculations are presented in Table 5. The accuracy of the model depends on how well the fermentation is defined in terms of what reactions are available in the system (what enzymes are present), the amount of ATP generated per reaction, the free energy of formation of each reactant and product, and the stoichiometry of the reactions. The free energy of formation is easily obtained from textbooks. The stoichiometry of reactions is generally clear for synthesis reactions from $CO_2$, CO and $H_2$. For example, Two $CO_2$ and 6 $H_2$ are needed to balance production of 1 ethanol ($C_2H_5OH$) and 3 $H_2O$. The number of ATP per reaction also varies and the fermentation system could enable more than one option for ATP production. Generally, degradation or synthesis of ethanol or acetic acid from or to gases only yields a fraction of an ATP (e.g. 0.2 ATP). Despite these uncertainties, the relative differences in the way each metabolite is affected by these conditions are clearly established.

Equilibrium concentrations were calculated to represent addition or removal of $H_2$ or increased total pressure of the fermentation (Table 5). These values may vary from observed values because of uncertainties of efficiencies, however the trends in concentrations relative to other metabolite concentrations depend on known stoichiometry, and thus are more certain. The predictions show, for example, the impact of adding or removing $H_2$ to establish new $H_2$ concentrations on methane production and acetate degradation or production. For example, removing $H_2$, as described in U.S. patents filed by the inventors, U.S. Ser. Nos. 12/000,856 and 60/871,441, is represented in the far left column and shows the greater degradation of acetic acid and capture of more energy as removed $H_2$ rather than $CH_4$ or other VFA. Increasing $H_2$ increases $CH_4$ production. The amount (moles) of $H_2$ removed or added can also be calculated from stoichiometry using the model. Although the effects on $CH_4$ production are opposite for increasing or decreasing $H_2$, acetic acid degradation increases for both effects. Thus, manipulating the ratio of $H_2$ to $CO_2$ is a means to shift fermentation toward degradation of acetate to methane or the opposite effect.

The far right columns show the effect of increasing the total gas pressures. The higher total pressure does not affect the pressure of $H_2$, but $H_2$ becomes a lower percentage of the total gas. This of course is the opposite effect of decreasing pressure using application of vacuum (U.S. Ser. Nos. 12/000,856 and 60/871,441). The equilibrium concentrations of acetic acid increase with higher total pressure. Thus, increasing pressure shifts the fermentation toward greater acetic acid production (either from $CO_2$ and $H_2$, or by decreasing degradation) rather than production of methane and $H_2$. The thermodynamic model readily demonstrates the effects of various manipulations. Furthermore, these manipulations can be used to select for a type of microbial activity, to isolate microorganisms with that activity, and to direct evolution. For example, gas pressures needed to select for bacteria that produce acetate from $CO_2$ and $H_2$ can be determined as shown.

The inventors isolated and used microorganisms that synthesize alkyl alcohols, such as ethanol, from $CO_2$ and $H_2$ or CO and $H_2$. The inventors demonstrated that not only is de novo synthesis (from $CO_2$ and $H_2$) a possibility, but also that degradation of acetic acid and ethanol can be carried out by the same microorganisms and the same enzymes. Whether ethanol or acetic acid are created from $CO_2$ and $H_2$ or degraded to $CO_2$ and $H_2$ depends on thermodynamics, and concentrations of reactants or products. If the partial pressure of gases is high relative to the concentration of ethanol or acetic acid, the equilibrium is shifted toward synthesis of ethanol or acetic acid rather than degradation.

Ways to Shift Fermentation Regarding Synthesis or Degradation of Acetate and Ethanol There are several ways in which the thermodynamic analysis shows it is possible to shift metabolism toward synthesis of a desired alcohol or acid. The first way is to change the pressure of all gases, for example to increase total gas pressures, so that the partial pressure of $CO_2$ and $H_2$ are affected. Increasing the partial pressure of all gases this way increases the concentration to which alcohols or acids can be synthesized from gases. Decreasing the partial pressure of all product gases increases the degradation of acetic acid or ethanol. The second way to increase synthesis of alcohols or acids is to adjust the ratio of synthesis gases to a ratio that favors a certain product, the higher ratio favoring alcohols over acids and longer-chain length acids or alcohols over the shorter. In addition, low pH also favors alcohols over acids.

Calculations of $\Delta G$ or equilibrium calculations can be used to quantify the effect of the ratio of $H_2$ to $CO_2$, the total pressure, and pH. The second law of thermodynamics enables calculation of which direction a pathway flows and whether energy is required or can be captured by carrying out the reaction. The relationship is determined by the sign and magnitude of the change in free energy ($\Delta G$) from the equation:

$$\Delta G = \Delta G° + RT \ln \{[\text{Products}]/[\text{Reactants}]\}$$

where [Products] or [Reactants] represents the multiplicative product of the concentrations or partial pressures of solutes or gases and $\Delta G°$ is constant for each reaction based on the products and reactants. When the $\Delta G$ is negative, the reaction can proceed and if it is negative enough, ATP can be generated.

TABLE 5

Selected equilibrium pressures and concentrations when partial pressures of gases are manipulated.

| Item | Total pressure = 1 atm | | | | | Total pressure = 2 atm | | |
|---|---|---|---|---|---|---|---|---|
| $CO_2$, atm | 0.95 | 0.75 | 0.50 | 0.25 | 0.05 | 1.90 | 1.0 | 0.10 |
| $CH_4$, atm | 0.05 | 0.25 | 0.50 | 0.75 | .95 | 0.10 | 1.0 | 1.90 |
| $H_2$, atm | $1.0 \times 10^{-4}$ | $1.6 \times 10^{-4}$ | $2.2 \times 10^{-4}$ | $2.8 \times 10^{-4}$ | $4.5 \times 10^{-4}$ | $1.0 \times 10^{-4}$ | $2.2 \times 10^{-4}$ | $3.8 \times 10^{-4}$ |
| Ac degradation if greater: | $2 \times 10^{-3}$ | $8 \times 10^{-3}$ | $1 \times 10^{-2}$ | $8 \times 10^{-3}$ | $2 \times 10^{-3}$ | $8 \times 10^{-3}$ | $4 \times 10^{-2}$ | $4 \times 10^{-3}$ |
| Ac synthesis if less: | $2 \times 10^{-6}$ | $9 \times 10^{-6}$ | $1 \times 10^{-5}$ | $9 \times 10^{-6}$ | $2 \times 10^{-6}$ | $9 \times 10^{-6}$ | $5 \times 10^{-5}$ | $4 \times 10^{-6}$ |

Model assumes pH = 6.5, temperature = 39° C. Ac = acetate, at 50 mmol/L. Assumes production of 0.2 mol interconversion of ATP with ADP per mol acetate synthesis or degradation.

The results in Table 5 demonstrate a means to control a mixed culture fermentation containing methanogens to produce more acetic acid and less methane by increasing pressure. Alternatively, acetate degradation can be increased by decreasing pressure or by increasing or decreasing the ratio of $H_2$ to $CO_2$. Decreasing $CO_2$ or increasing $H_2$ can shift the fermentation toward making more methane and degrading the acid.

Another way to represent the direction or feasibility of reactions is to calculate the equilibrium concentration of a product. Additional product can be feasibly accumulated if it the concentration is less then the equilibrium concentration, or the product will be degraded if the concentration is less than the equilibrium concentration. The equilibrium concentration is calculated by setting the $\Delta G$ to 0 and solving the equation for the concentration of products. The $\Delta G$ may include the ΔG for ATP generation if it is known or presumed to support microbial growth. This approach was used to show the effect of pressure, ratio of $H_2$ to $CO_2$ and pH on the concentration of alcohols and carboxylic acids. For the following reactions:

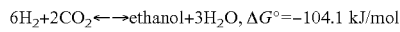

$$6H_2 + 2CO_2 \leftrightarrow \text{ethanol} + 3H_2O, \Delta G° = -104.1 \text{ kJ/mol}$$

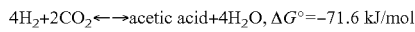

$$4H_2 + 2CO_2 \leftrightarrow \text{acetic acid} + 4H_2O, \Delta G° = -71.6 \text{ kJ/mol}$$

The feasible concentration of acetate equals $e^{(\Delta G° - \Delta GATP)/RT} \times [H_2O]^2 [H^+] \times [H_2]^4 [CO_2]^2$. The ([$H^+$] is equal to $-\log_{10}$ pH, and [$H_2O$] was assumed to be 50 mol/L. The result depends on the amount of ATP produced. In this example, free energy for ATP was assumed to be 44 kJ/mol of acetate produced. The feasible concentration of ethanol equals $e^{(\Delta G - \Delta GATP)/RT} \times [H_2O]^3 \times [H_2][CO_2]^2$. Feasible (or equilibrium) ethanol concentration does not depend on pH. ATP was again assumed to be 44 kJ/mol of ethanol produced. Equilibrium concentrations of other alcohols and acids were determined in a similar manner solving for the concentration of each carboxylic acid or alcohol under different pressures or ratios of $H_2$ and $CO_2$.

As longer VFA and alcohols include additional synthesis steps, the number of ATP (and therefore kJ/mol captured) was assumed to be greater by 1 ATP (44 kJ/mol) for each elongation step. For example, synthesis of propionate or propanol was assumed to capture 2 ATP (88 kJ/mol), and synthesis of butyrate or butanol was assumed to capture 3 ATP (132 kJ/mol). These values reflect the steps known for ATP capture in the pathways for interconversion.

Figure 4:
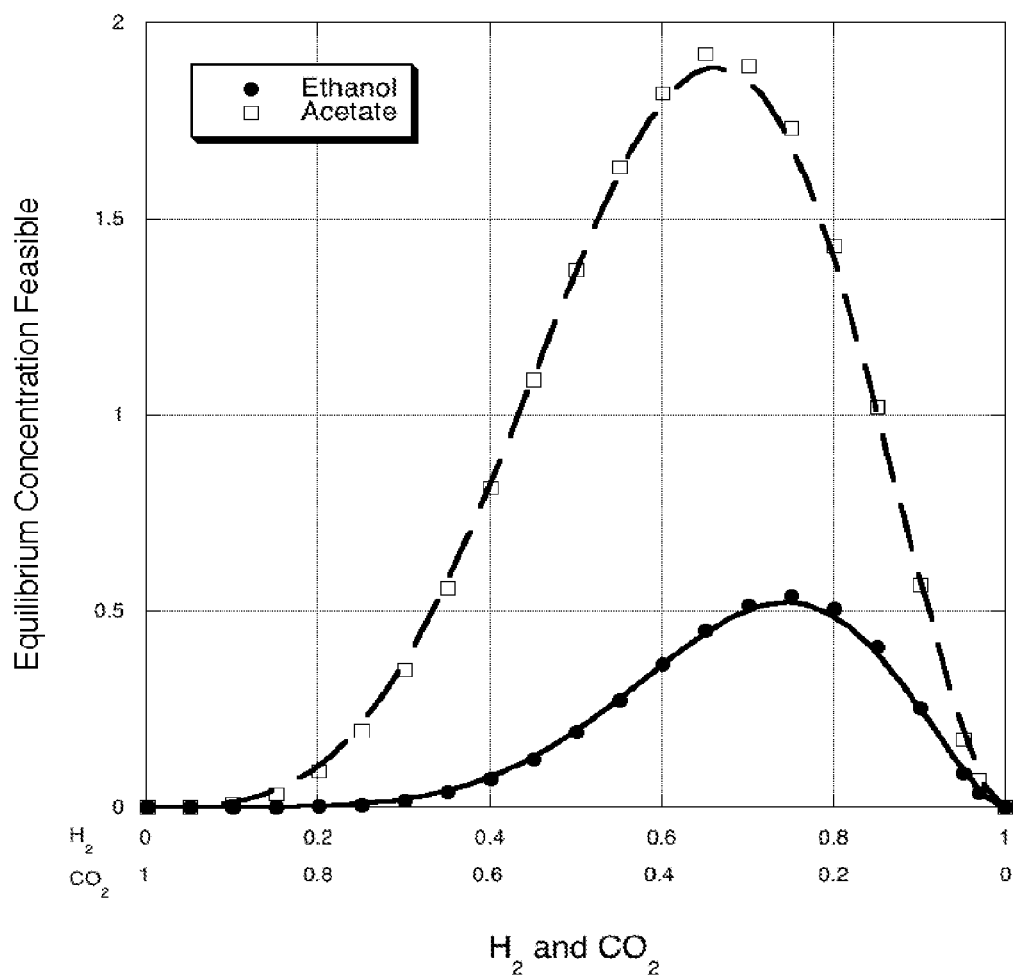
FIG. 4 indicates the calculated equilibrium concentration (mol/L) of ethanol or acetate at pH 4 where partial pressure of hydrogen ($H_2$) increases with constant total gas pressure of 1 atm comprising $H_2$ and carbon dioxide ($CO_2$) gas. This figure shows that microorganisms would have limited capacity to obtain energy from synthesizing ethanol from synthesis gases at 1 atm total pressure, and ethanol and acetate synthesis are favored over degradation at specific ratios of $H_2$ to $CO_2$.

The equilibrium concentration of ethanol or acetic acid synthesis relative to degradation at a constant total pressure is shown in FIG. 4. If the total gas pressure is maintained at 1 atm, as the $H_2$ pressure increases from 0 atm to 1 atm, the $CO_2$ partial pressure will decrease from 1 atm to 0 atm. The estimated peak concentrations of acetate or ethanol would occur when the ratio of $H_2:CO_2$ is 2:1 for acetic acid, and 3:1 for ethanol (FIG. 4). Although temperature and total pressure affects the extent to which ethanol or acetic acid can be concentrated, the ratios of gases to maximize the concentrations of ethanol or acetic acid under any given set of conditions is constant. One way to increase ethanol synthesis from gases, is therefore to add or retain either $CO_2$ or $H_2$, or remove or utilize $CO_2$ or $H_2$ to leave gases in the corresponding ratio for maximal synthesis. A way to increase degradation of ethanol or acetic acid is to manipulate $CO_2$ or $H_2$ away from the ratios for maximal synthesis by either increasing or decreasing $CO_2$ or $H_2$.

Figure 5:
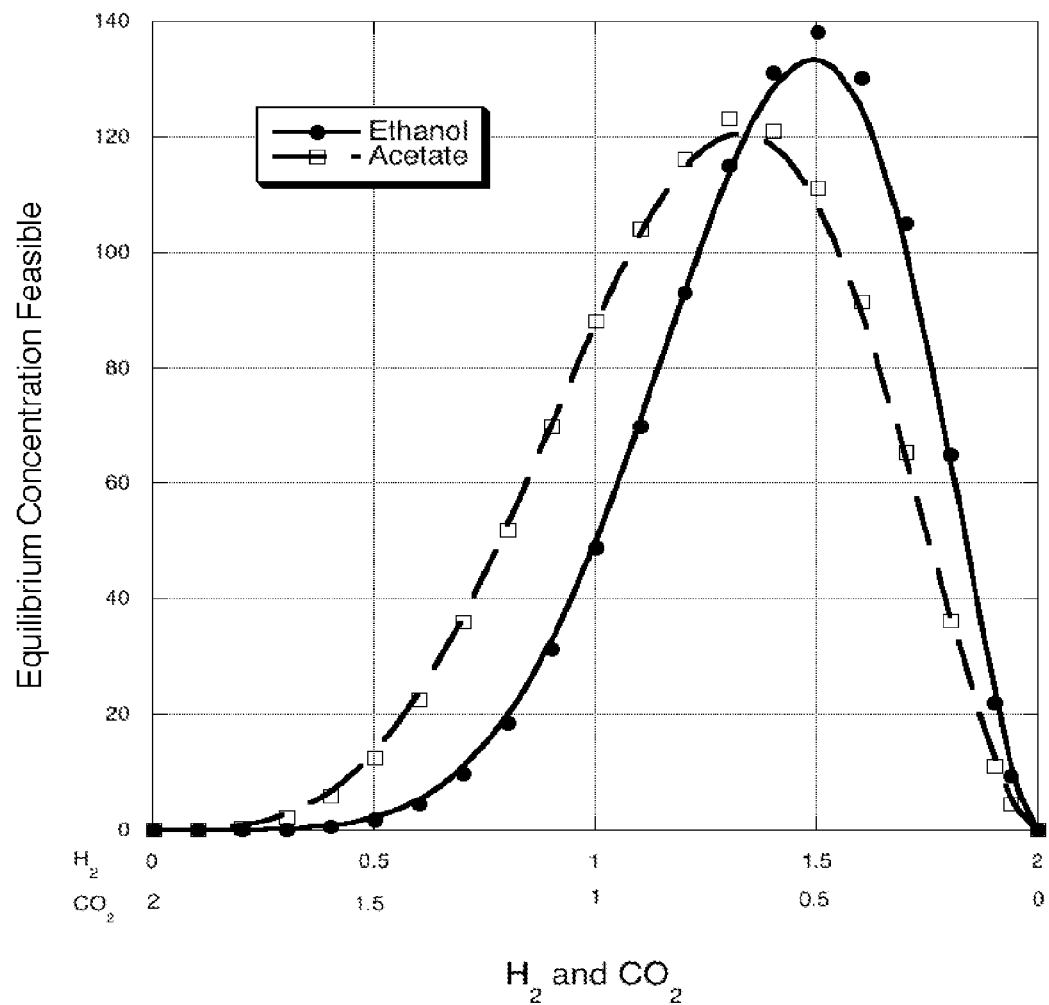
FIG. 5 indicates the calculated equilibrium concentration (mol/L) of ethanol or acetate at pH 4 where partial pressure of hydrogen ($H_2$) increases with constant total gas pressure of 2 atm comprising $H_2$ and carbon dioxide ($CO_2$) gas. This figure shows that microorganisms would have greater capacity to produce ethanol or acetic acid when under pressure especially when the ratio of $H_2$ to $CO_2$ is 2:1 or 3:1 for acetate or ethanol respectively.
Figure 6:
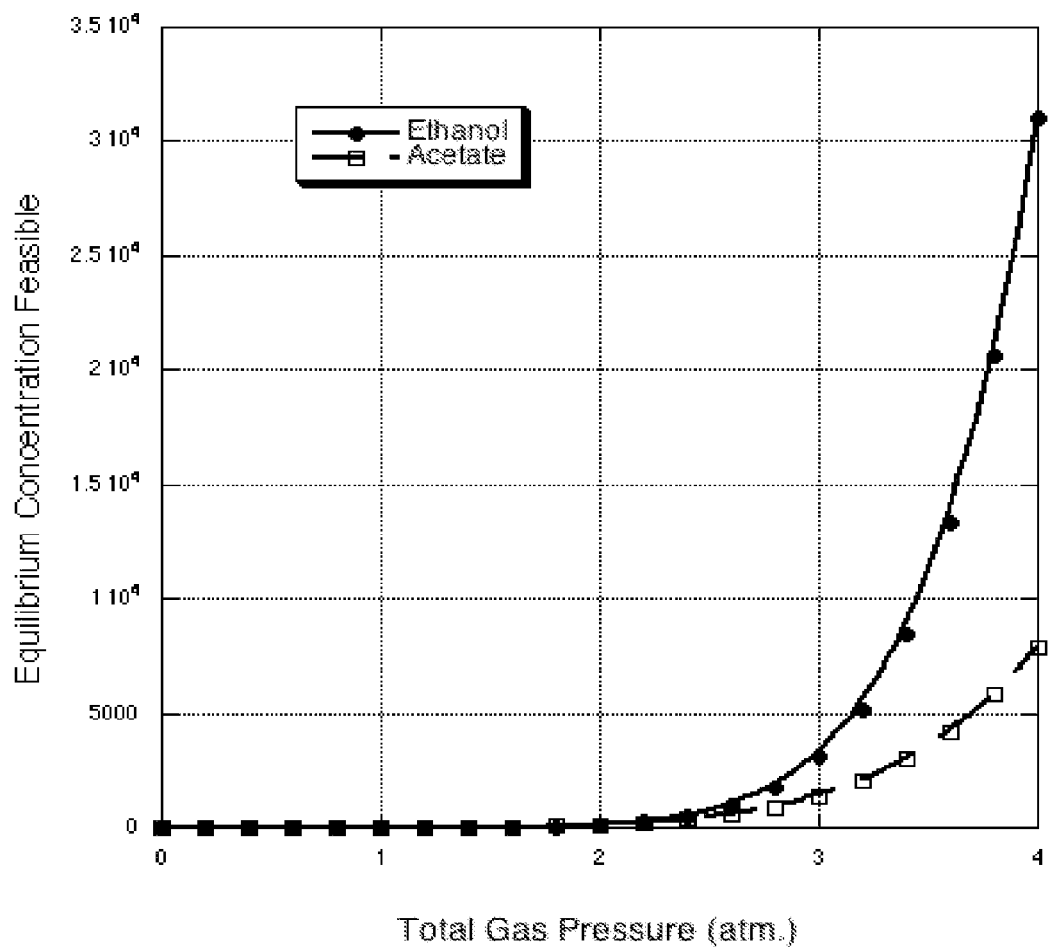
FIG. 6 indicates the equilibrium concentration of ethanol or acetate at pH 4 where total pressure of all gases is increased and gases are comprised of a constant ratio of 75% $H_2$ and 25% carbon dioxide ($CO_2$). This figure shows the greater feasibility to make higher concentrations of ethanol at higher pressure.
Figure 7:
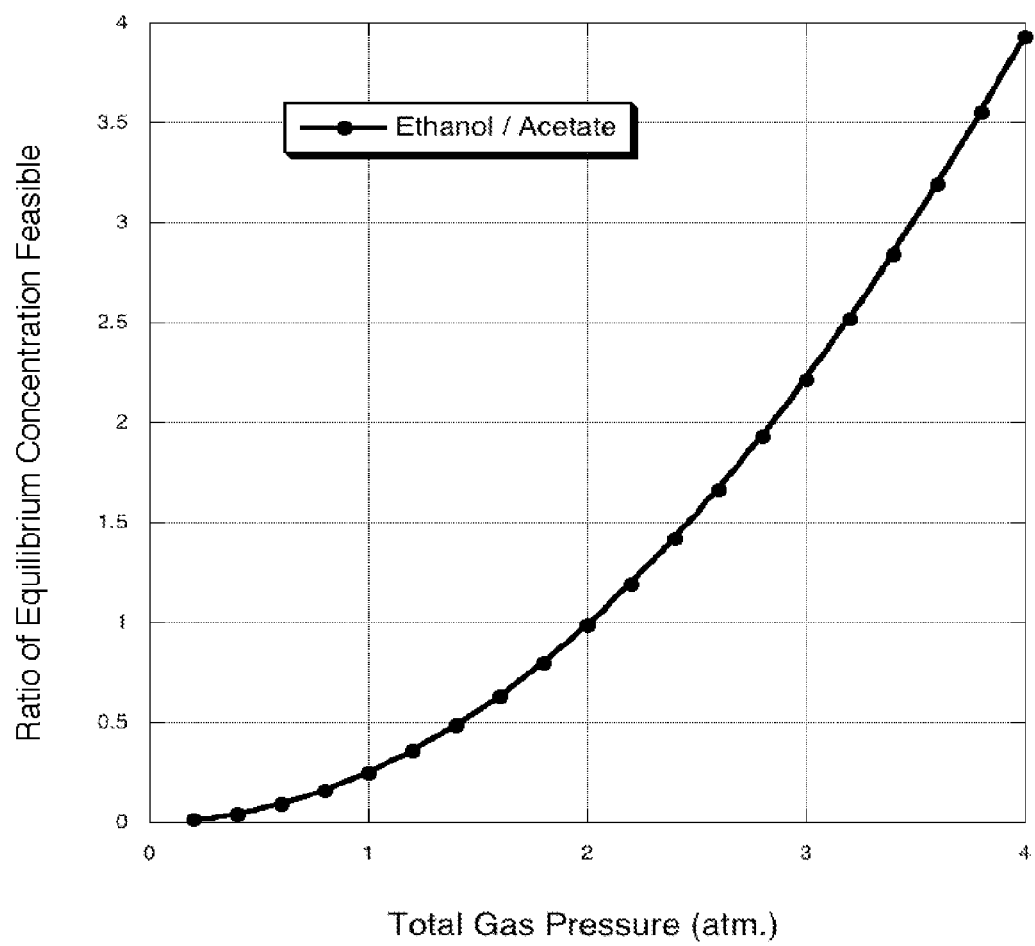
FIG. 7 indicates the ratio of equilibrium concentrations of ethanol to acetate at pH 4 where total pressure of all gases is increased and gases are comprised of a constant ratio of 75% $H_2$ and 25% carbon dioxide ($CO_2$). This figure shows the shift from the acid to alcohol production when greater gas pressures are used.

Thermodynamics also shows that increasing total gas pressure is a means to increase both $CO_2$ and $H_2$ partial pressures, thereby increasing synthesis over degradation of ethanol or acetic acid. Concentrations of both ethanol and acetic acid that can be synthesized increase exponentially as the total gas pressures increase at a constant ratio of $H_2$ to $CO_2$ (FIGS. 5 and 6). However, exponent is 8 for ethanol and 6 for acetic acid corresponding to the stoichiometry of ethanol and acetic acid synthesis, which requires 8 or 6 moles of gas respectively to produce ethanol or acetic acid. Thus, the effect of pressure is exponentially greater for ethanol synthesis than for acetic acid synthesis (FIG. 7), where the exponent is 2. In other words, increasing total gas pressure when the gases are comprised of a similar concentration of $CO_2$ and $H_2$, shifts metabolism toward synthesis of both ethanol and acetic acid, but also shifts metabolism toward ethanol relative to acetic acid.

The feasible concentration predicts only the acetate form, not the conjugate acid. But at neutral pH most of the acetic acid and acetate is in the acetate form. At near neutral pH, the thermodynamically feasible concentrations are high for carboxylic acids. For example, assuming 1 ATP produced per mole of acetate produced, pH 6.5, and 1 atm of $H_2$ and $CO_2$ in the ratio for maximal acetate synthesis, peak acetate yield at equilibrium could be 442 M when solving for the equilibrium concentration using the ΔG equation. This is far beyond the number of moles that could fit in the space indicating that there would be no thermodynamic limit to acetate production under these conditions. If the pH in the above example is decreased to 4, the acetate production would be limited to about 1.4 M (and a slightly greater amount of the acetic acid form would also be produced), but the ethanol concentration would not be affected by pH.

These discoveries can be applied to increase the efficiency of ethanol production from $CO_2$ and $H_2$, by using high total pressures to increase the ethanol concentration that can be derived from gases. It can also be used to enrich or select for microorganisms that synthesize ethanol rather than acetic acid, or to control microbial cultures that have access to both pathways. The inventors found empirically that when incubating with two atmospheres $H_2$ pressure, organisms were isolated that decreased total gas pressure while they fermented cellulosic substrate. These organisms synthesized additional ethanol from the added $H_2$ and the $CO_2$ released from degradation of cellulosic biomass to ethanol. The inventors also isolated organisms under conditions favoring ethanol production (4 atmospheres, ratio of $H_2:CO_2$ of 3, and those organisms produced a higher molar concentration of ethanol than acetate. In particular, isolates obtained after enrichment in pH 5 media produced more ethanol than isolates enriched on pH 7 media.

In an industrial process, most of the gases will be able to be converted to ethanol, rather than acetate, if conditions do not favor acetate production or if the microbes that make ethanol do not make acetate. Both of these are possibilities. If acetate is allowed to build up initially, it inhibits further acetate production as ethanol is produced. The acetate can be maintained in the fermenter as ethanol is removed (distilled out), or both can be removed and used separately. On the other hand, growing organisms under conditions that disfavor acetate production selects against acetate producers and eventually provides organisms with impaired ability to produce acetate. In studies conducted by the inventors, some isolated organisms produced a much higher molar ratio of ethanol to acetate than others even when isolated under the same conditions. This suggests the ability for the microbes to adapt to producing ethanol making it less critical to always maintain those conditions to continue producing ethanol.

Thermodynamics for Synthesis from $H_2$ and CO

The same principles can be applied to mixtures of $H_2$ and carbon monoxide (CO). Similar calculations based on stoichiometry can be used to quantify that the ratio of $H_2$ to CO for maximal synthesis is 2:1 for ethanol or 1:1 for acetic acid. The effect of increasing pressure is the same as for synthesis of ethanol or acetic acid from $H_2$ and $CO_2$. Thus, adjusting gas formulations and increasing pressures would also shift metabolism toward greater ethanol synthesis or acetic acid synthesis when using CO and $H_2$ as well, or when selecting for microorganisms that can use these gases. The inventors discovered that organisms selected to produce products from $CO_2$ and $H_2$ produced a similar profile of products from CO and $H_2$.

Thermodynamics for Synthesis of Other Alcohols

Figure 8:
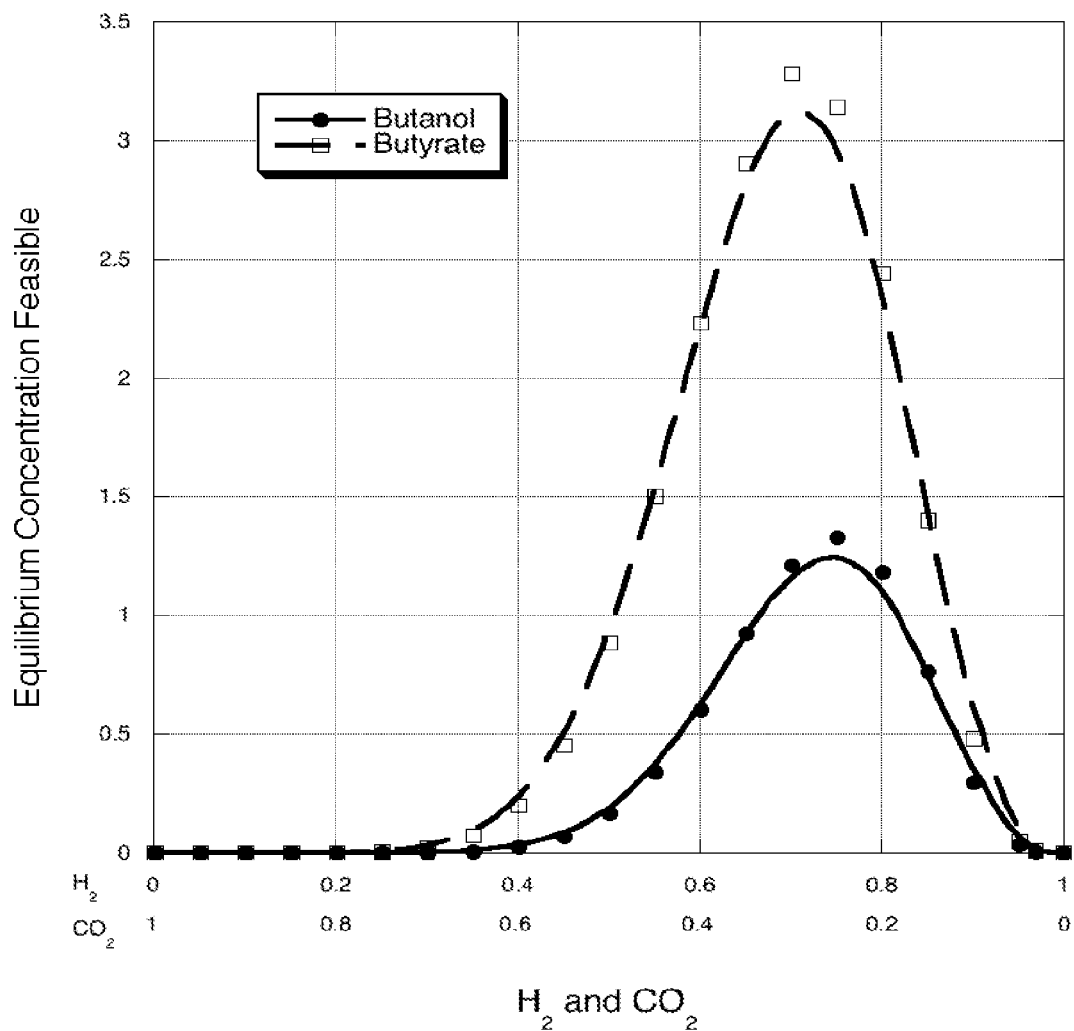
FIG. 8 indicates the equilibrium concentrations (mol/L) of butyrate and butanol at pH 4 where partial pressure of hydrogen ($H_2$) increases with constant total gas pressure of 1 atm comprising $H_2$ and carbon dioxide ($CO_2$) gas. This figure shows the ratio for maximal butyrate or butanol synthesis.
Figure 9:
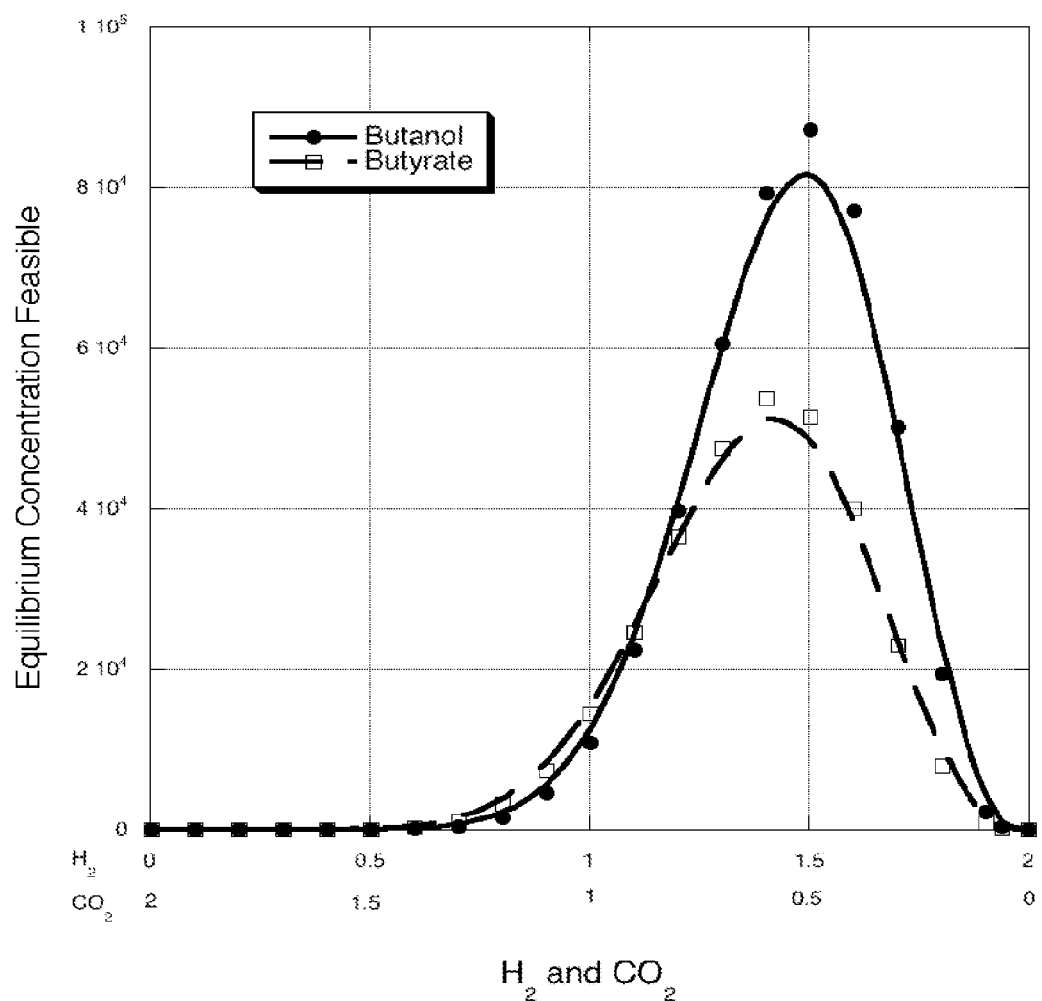
FIG. 9 indicates the equilibrium concentrations (mol/L) of butyrate and butanol at pH 4 where partial pressure of hydrogen ($H_2$) increases with constant total gas pressure of 2 atm comprising $H_2$ and carbon dioxide ($CO_2$) gas. This figure shows the dramatic effect on equilibrium ratios of products as the pressure is increased.

These principles were also applied to determine the optimal ratios for butanol or butyrate synthesis (FIG. 8). The optimal ratio of $H_2$ to $CO_2$ is 3:1 for butanol production or 5:2 for butyrate production. Increasing total pressure at a constant ratio of gases increases butanol and butyrate equilibrium concentration, and butanol concentration relative to butyrate (FIG. 9). The optimal ratio of $H_2$ to CO for butanol synthesis was 2:1, and the optimal ratio of $H_2$ to CO was 3:2 for butyrate synthesis. The effect of pressure was similar for $H_2$ and CO as for $H_2$ and $CO_2$.

Controlling the ratio and total pressure of $H_2$ and $CO_2$ favors long-chain alcohols and long-chain acids over acetate. For example, at twice the pressure (2 atm vs. 1 atm) the equilibrium concentration of acetate increases 70 fold, but the equilibrium concentration of ethanol increases more than 250 fold. These values were calculated from the peak results of FIGS. 4 and 5, by comparing the peak reactant concentrations at the higher pressure to those at the lower pressure. At 2 atm pressure of total gases, the equilibrium concentration of butyrate would increase 17,000 fold over 1 atm (compared to 70 fold for acetate), and the equilibrium concentration of butanol would increase 80,000 fold over the concentration at 1 atm. Thus, it is apparent that the effect of pressure and ratio of $H_2$ to $CO_2$ is much more important for alcohols over the corresponding acids, and for longer chain alcohols or acids over the shorter chain length.

Figure 10:
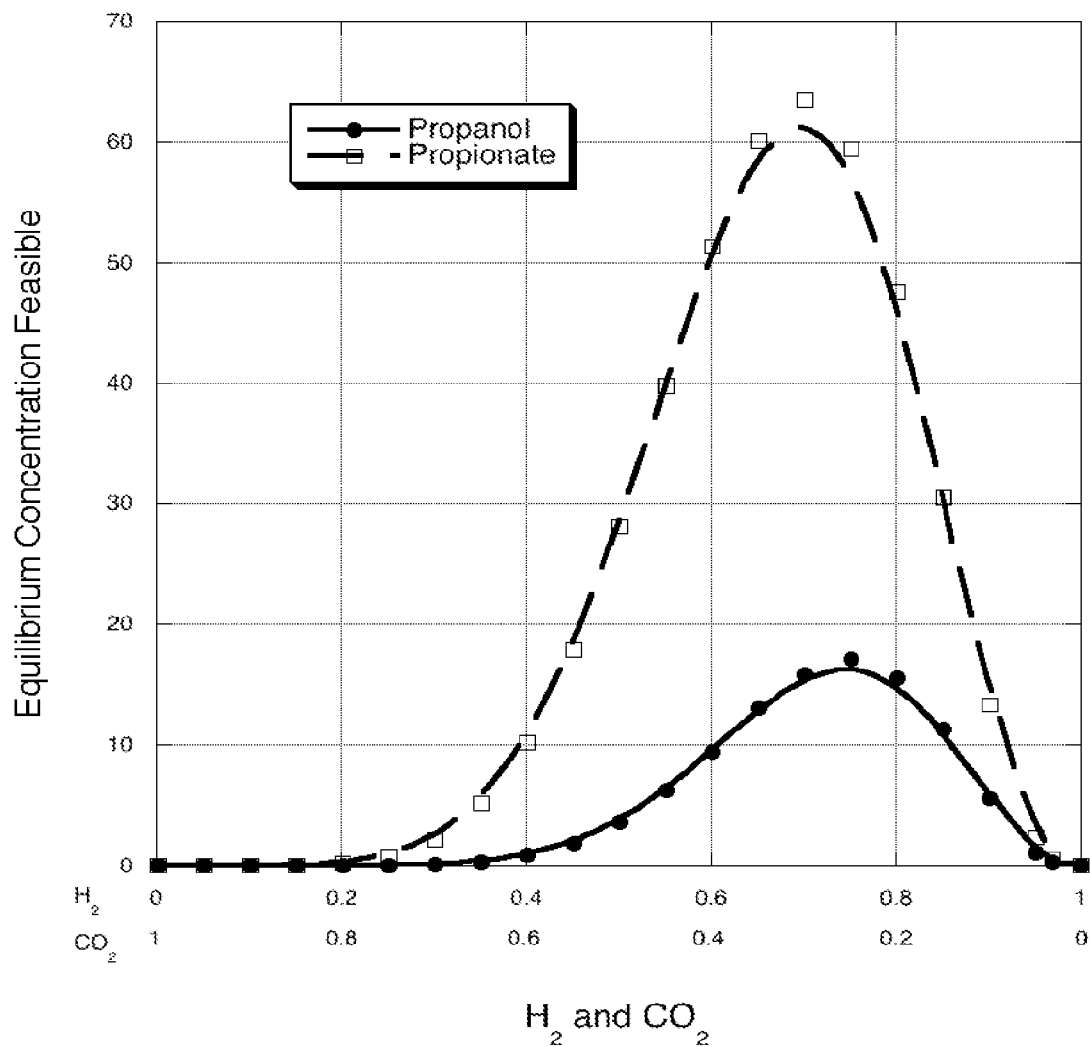
FIG. 10 indicates the equilibrium concentrations (mol/L) of propionate and propanol at pH 4 where partial pressure of hydrogen ($H_2$) increases with constant total gas pressure of 1 atm comprising $H_2$ and carbon dioxide ($CO_2$) gas. This figure shows the optimal ratio for propionate and propanol synthesis from synthesis gases.

These principles also apply to synthesis of propanol and propionate from gases. The optimal ratio of $H_2$ to $CO_2$ is 3:1 for propanol synthesis or 7:3 for propionate synthesis (FIG. 10). Increasing total pressure at a constant ratio of gases increases concentration where propanol and propionate synthesis occur and increases concentration where degradation occurs, and increases possible propanol concentration relative to propionate. The optimal ratio of $H_2$ to CO for propanol synthesis was 2:1, and the optimal ratio of $H_2$ to CO was 4:3 for butyrate production. The effect of pressure was similar for $H_2$ and CO as for $H_2$ and $CO_2$.

In every case, increasing gas pressures shifted metabolism toward higher synthesis concentrations, and away from degradation, and toward greater alcohol compared to the analogous volatile fatty acid concentration. The actual calculated concentrations are the optimal mixtures of gases for each of these synthesis reactions, and one aspect of the invention is the use of thermodynamics and stoichiometry to calculate optimal ratios of gases for synthesis of desired products. Another aspect is the application of total gas pressures, such as greater than 1 atm or more, to increase the concentrations that alcohols or acids when produced from gases. This concept can be applied to any fermentation reaction in which a greater number of moles of reactant gases are used to produce a lower number of moles of product gases, and the reaction, like many fermentation reactions, is near equilibrium.

Providing partial pressures of gases that make it thermodynamically feasible to produce a high concentration of carboxylic acids with greater than 2 carbons (e.g. $C_3$ to $C_{20}$) or to produce a high concentration of alcohols, is not likely to be achieved reliably without understanding and calculating the thermodynamic constraints. Simply adding $H_2$ or $CO_2$ to the reactor would shift the fermentation toward one or the other ends of the diagrams in FIGS. 4 to 5 and 8 to 10, and result in degradation of the alcohols or longer-chain acids at least some of the time. Applying higher pressure without providing the correct ratio of gases would also be futile. Only through using the thermodynamic analysis and with use of microorganisms that are selected through this process, is it possible to consistently produce the desired products at a high concentration. For this reason, microbes have not been previously isolated that are known to produce the significant quantities of longer chain acids or alcohols from $CO_2$, CO and $H_2$ and previous investigators have not been able to produce high concentrations of either acids or alcohols from the gases.

When a ratio of $H_2$ to $CO_2$ is perfused into the incubation that is not optimal for the desired end product, one of two events must occur: 1) the metabolism will shift in order to use the excess gas, or 2) the accumulation of the desired product will stop because the gas mixture will shift toward a greater concentration of the excess gas as the limiting gas is used up. The first case occurs when an alternative pathway is available, and it will result in production of undesired product rather than the desired product. The second case would be especially limiting for microbial cultures with limited options to shift to different end products. These organisms would appear to be intolerant to high concentrations of the product they produce. In fact, they would be limited thermodynamically at one end or the other of the previous graphs 4 to 5 and 8 to 10 (i.e. low $CO_2$ or low $H_2$). One means to select for organisms to produce a desired product from synthesis gases is to maintain the optimal ratio of gases for the desired product.

Furthermore, the thermodynamics described above led to a better understanding of what type of microbial activity is needed to produce alcohols from $CO_2$, CO and $H_2$. Wherein, production of high concentrations of alcohols is promoted by moderately low pH (e.g. pH 4 to 5) and high pressures of $H_2$, organisms that can tolerate these conditions were isolated. Using the partial pressures of $H_2$ and $CO_2$ to favor alcohol production or longer chain carboxylic acid production resulted in isolation and use of microbes that could produce ethanol, 1-propanol, or 1-butanol in the presence of a high concentration of these alcohols. For example, microbes produced ethanol from synthesis gases in the presence of more than 10% ethanol concentration.

Thermodynamics for Synthesis of Carboxylic Acids

Just as the conditions to favor synthesis of alcohols of different length were established through the previous analysis, the approach can also be applied to produce volatile fatty acids (e.g. $C_2$ to $C_5$), or even longer-chain carboxylic acids. The $\Delta G$ values shown in FIG. 3 demonstrate the potential for producing carboxylic acids of increasing length by using a ratio of $H_2$ to $CO_2$ to make production of desired carboxylic acids feasible or more favorable than competing products. The minimal $\Delta G$ for acetate production from $H_2$ and $CO_2$ occurs at 2:1 $H_2$ to $CO_2$ ratio, but the minimal $\Delta G$ for longer carboxylic acids occurs at a slightly higher ratio (up to 3:1). The thermodynamics of longer carboxylic acids is also favored by increasing total pressure and lower pH favors longer chain acids over the shorter ones. These are precisely the conditions in which organisms that mainly produce longer chain acids like butyrate and iso-valerate were isolated. The inventors measured free carboxylic acids as long as caproic acid ($C_6$) from mixed rumen fluid so these longer acids can be produced and excreted from the organisms. Typically, these carboxylic acids would not be produced in a natural fermentation, but they can be produced if the ratio of $H_2$ and $CO_2$ is increased above natural conditions.

It is clear from FIG. 1, that the conditions of pressure and gas composition for acetate production are not as stringent as for longer chain carboxylic acids or alcohols. However, it is helpful to maintain adequate $CO_2$ and $H_2$ pressure and pH>4 or more preferably greater than 5. Producing acetic acid as a feedstock for another process or as a product it self is one of the easiest organic compounds to synthesize from gases under typical fermentation conditions. In fact, it may be useful to recover gases that have low $CO_2$ or $H_2$ composition by converting the gases into acetate. For example, gases with too little $H_2$ to be worthy of separation in a cost efficient manner, or gases from fermentation or combustion could be used. The waste gases may be pressurized to make it possible to use skewed ratios or low percentages of $H_2$ or $CO_2$. It may be helpful to maintain to maintain neutral pH for the process, but some organisms are acid tolerant. Alternatively, this analysis shows how to limit acetate production thermodynamically by decreasing pH.

The thermodynamic analysis further shows that greater care needs to be taken to establish conditions for alcohol or longer-chain carboxylic acid production. In fact, it is unlikely that very high concentrations of ethanol can be produced without understanding the exact conditions of pressure and gas composition that are needed. In addition, one needs to understand the exact conditions to disfavor acetate production (e.g. low pH) to limit its production. Finally, microbes to produce longer alcohols require even more exact conditions, including pressurization above 1 atm and potentially above 2 or 3 atm and a ratio of $H_2$ to $CO_2$ (e.g. 3) or $H_2$ to CO (e.g. 2) that maximizes production of the longer-chain acids or alcohols. When these conditions were applied, the inventors isolated microbes that made significant concentrations of these alcohols (ethanol, 1-propanol, 1-butanol), and various lengths of carboxylic acids ($C_2$ to $C_5$) that were enriched for, selected, and used to make desired products.

Certain Embodiments of the Invention

The process described herein comprises using multiple simultaneous equations to calculate ΔG for all possible reactions in a fermentation system for production of organic compounds from $H_2$, $CO_2$, and/or CO. The mathematical model differs from models used previously in that multiple simultaneous equations are used and solved to identify the optimal conditions to isolate and develop organisms and conduct the fermentation. By using simultaneous equations, it is possible to determine conditions that make desired pathways thermodynamically favorable compared to competing pathways, and therefore to shift the fermentation in the desired direction.

The models indicate the composition of gases (e.g. $CO_2$, CO and $H_2$) necessary to make production of high concentrations of certain alcohols or acids thermodynamically feasible or favorable, and these conditions are used in conjunction with other information to isolate, develop and use microorganisms for optimal production of various alkyl alcohols and carboxylic acids. The models and empirical results also show the advantages of pressurizing the fermentation above 1 atmosphere for producing a higher concentration of the desired product. Many other conditions such as temperature, pH, and concentrations of metabolites further improve the fermentation toward desired results. All of these manipulations are aspects of the process, however, the process also embodies more than each of these individual manipulations.

The process involves manipulation of the gases and other products (e.g. alcohol concentration, carboxylic acid concentration) and temperature in concert with each other to direct the fermentation to produce desired products. Although many different sets of conditions can be used, this application shows how to evaluate and optimize appropriate sets of conditions for a certain product concentrations. For example, the model can be used to develop conditions that make it thermodynamically favorable to produce certain concentrations of desired products. Thus, rather than prescribe a certain ratio of gases or a certain pressure of the fermentation, the process described in this application enables the user to determine the optimal ratio of gases, pressure and other factors that are needed together to obtain the desired results. For example, the model can determine if it is more cost effective to pressurize the system than to adjust the ratio of gases.

No previous investigator has been able to make high concentrations of alcohols or carboxylic acids, or to shift fermentation toward certain products, because they have not used all of the conditions required to make it thermodynamically feasible, and certainly not thermodynamically favorable, to produce those products. Although it is sometimes possible to occasionally achieve the appropriate conditions by coincidence to produce some products, the thermodynamic model makes it possible to consistently produce the product in high concentration and to maintain the organisms that produce it. Without understanding thermodynamic aspects of fermentation, it is impossible to consistently produce alcohols or longer chain carboxylic acids from synthesis gases.

Existing processes using current microorganisms may be improved by using the defined process conditions from this application to make greater concentrations of alkyl alcohols or carboxylic acids, but it would be especially advantageous to use the process conditions described in this application with microorganisms that are isolated or developed using the process described in this application. Conditions were described and used to enrich for microorganisms that produce the desired alcohols or carboxylic acids from $H_2$, $CO_2$, and CO. Conditions were established to isolate microbial isolates on the basis of the products they produce because the conditions are such that organisms that produce certain products are favored. In addition, the model is used to establish conditions that can be used to select from mutants that produce more of the desired products, or a higher rate of production, or less of an undesired product. In this way, the conditions improve microorganisms making them better able to produce a desired product. The microorganisms that were isolated and developed as an aspect of this application can produce high concentrations of ethanol, such as more than 10% ethanol by volume, from $CO_2$ and $H_2$ or CO and $H_2$. Isolates were also isolated that were tolerant to 6% propanol and 6% butanol and that produced 1-propanol and 1-butanol. Some of the isolates were aerobic or aerotolerant, offering certain advantages of handling.

Although many variations are possible to produce products from various sources of gases ($CO_2$, CO, and $H_2$), key features of this invention include the simplifications of the procedure commonly used, ability to use lower concentrations of gases, ability to obtain greater concentrations of the desired products at higher rates, and ability to obtain some products that have not been obtained previously from synthesis gases.

There are several novel aspects of the process described in this application including but not limited to those aspects summarized below. Several microorganisms were isolated that convert hydrogen gas and carbon dioxide gas or carbon monoxide gas and hydrogen gas to ethanol in aqueous media wherein ethanol concentration exceeds 4% by volume. These microbes were found to be tolerant to more than 10% ethanol by volume and to grow and produce additional ethanol under these conditions. The microbes also tolerate more than 1% acetate, and preferably more than 2 to 3% acetate in the fermentation media. In some cases multiple isolates of organisms can be used together or pure cultures of individual isolates can be used. In some cases, the amount of ethanol produced was greater than the amount of acetic acid produced on a molar basis. Many of the isolates were tolerant to oxygen, and at least one isolate was identified as a member of the genus, *Enterococcus* by 16S rRNA sequence. It had greater than 99% homology with *Enterococcus avium*. Many of the isolated microorganisms produced ethanol and grew at a pH less than 5, and sometimes less than pH 4.

A method was described for producing ethanol from hydrogen gas and carbon dioxide gas or from hydrogen gas and carbon monoxide gas or a combination of both. In this method, the ethanol concentration could exceed 4% by volume in aqueous media, but could also exceed 7% or 10% by volume. The method may comprise pressurizing the reaction vessel to greater than 1 atm, or even greater than 2 atm total gas pressure. In the method, the ratio of hydrogen to carbon dioxide in volume may be greater than 2 to 1 or more preferably greater than 3 to 1. The ratio of hydrogen to carbon monoxide would be greater than 1 to 1 or more preferably greater than 2 to 1. Under these conditions of pressure and ratio of gases, and other conditions of temperature and ethanol concentration, the ΔG for ethanol production is less than 0 even as the ethanol concentration increases. The pH in the fermentation may be less than 7 or more preferably less than 5, and it may even be less than 4. Under these conditions of pressure and ratio of gases, and conditions of pH and ethanol and acetate concentration, the ΔG for ethanol production may be more negative than the ΔG for acetate production, thus making it more favorable to produce ethanol than acetic acid.

A method described in the current patent application makes it possible to isolate an alcohol-tolerant microorganism to produce a lower alkyl alcohol from hydrogen gas, carbon dioxide gas, and/or carbon monoxide gas. In the described method, a mixed culture of microorganisms may be inoculated to media with a high concentration of at least one lower alkyl alcohol. The concentration of reactants and products is controlled to make production of the lower alkyl alcohol thermodynamically feasible. The total gas pressure may be greater than 1 atmosphere. In this process, the microorganisms may be enriched by growing them under conditions that favor degradation of the alkyl alcohol, and then conditions may be changed to select organisms that can also produce the desired alkyl alcohol. The lower alkyl alcohol may be ethanol, propanol, or butanol or a combination thereof. The method can produce a concentration of the alcohol greater than 6% by volume, or preferably greater than 10% by volume, or greater.

A method is also described for producing at least one lower alkyl alcohol from hydrogen gas, carbon dioxide gas and/or carbon monoxide gas in aqueous media, wherein the concentration of lower alkyl alcohols increases to greater than 4% by volume of the aqueous media. In this process the lower alkyl alcohol can be ethanol, propanol or butanol, or a combination thereof. The alcohol or alcohols may be separated from the aqueous medium by distillation including vacuum distillation, which does not kill the microorganisms, or by distillation creating steam. The production of alcohols may be created by incubation at a temperature greater than 35° C. or more preferably greater than 40° C. It can also be conducted at a higher temperature such as 55° C. or higher. The gas pressure may be greater than 1 atm, or more preferably be greater than 2 atm or even more preferably greater than 3 or 4 atmospheres. The partial pressures of hydrogen gas and carbon dioxide gas can be adjusted to make it thermodynamically more favorable to produce the desired alcohols over other products and over degradation of alcohols. The ratio of gases $H_2$ to $CO_2$ may be greater than 1 or more preferably greater than 2. Even more preferably the ratio can be greater than 3. A ratio of 3 is optimal to produce a higher concentration of alcohol by volume, but a ratio greater than 3 further favors alcohol production over corresponding carboxylic acid production. With all of the conditions of partial pressures and concentrations of products, it may be thermodynamically feasible to produce the alcohols to greater than 4% concentration of the aqueous media by volume. Volatile fatty acids may also be produced as a co-product and removed from the aqueous media. The volatile fatty acids may be removed by precipitating the conjugate base using addition of a divalent cation. For example, calcium or magnesium ions may be added by adding a salt or a base containing the ions. Precipitation may be aided by increasing the pH.

This application also describes a method for producing one or more volatile fatty acids from hydrogen gas, carbon dioxide gas and/or carbon monoxide gas using at least one microorganism under conditions that favor synthesis of the desired volatile fatty acids over degradation. The concentration of the volatile fatty acids may be greater than 1% concentration by volume. Preferably, the concentration may exceed 2% or 3% by volume. The volatile fatty acid may be acetic acid or acetate. It may also be a longer chain acid such as propionic acid or propionate, butyric acid or butyrate, iso-butyric acid or iso-butyrate, valeric acid or valerate, isovaleric acid or isovalerate. It could also be lactic acid or lactate, or succinic acid or succinate. It could be a longer-chain carboxylic acid such as caproic acid, caprylic acid, or capric acid. It could be a mixture of carboxylic acids or a single species of carboxylic acid may comprise more than 50% of the total carboxylic acid produced by molar proportion. For example, it may be more than 50% butyric acid by molar proportion. The pH of the fermenter may be adjusted to between 5 and 7 to increase production of carboxylic acids. The pressure in the fermenter may be greater than 1 atm or more preferably may even be greater than 2 atm. With low concentrations of $CO_2$, CO and $H_2$ or a skewed ratio of gases, the pressure may actually exceed several atmospheres in order to produce an adequate partial pressure of the gases to make it thermodynamically feasible to produce the desired carboxylic acids. The microorganisms used in the process may be rumen microorganisms in pure culture or an undefined mixed culture. The one or more volatile fatty acids can be precipitated as the conjugate base using a divalent cation. For example, an ionic form of calcium or magnesium may be used, or a different cation. The pH of the aqueous medium may be increased to favor precipitation of the salt of the carboxylic acid. The rate of carboxylic acid production may be greater than 5 mM per liter per day. Preferably it may even be greater than 10 mM per liter per day. The carboxylic acid may be used as an animal feed. Microbial protein produced in the process may also be used as an animal feed.

Identification of an Example Microorganism

The phylogenetical relationship to other microorganisms was determined for one exemplary organism by base-pair sequence of the 16S ribosomal RNA. The isolate was selected as one of the early ones to produce a high concentration of ethanol at a high rate from synthesis gases. The organism was purified an additional time using a streak plate and its fermentation properties confirmed after the secondary purification. An identical colony was submitted for colony PCR and sequenced (Sequence ID No. 1, below) on an automated sequencer. The sequence was compared against a library and identified as having 99.89% homology (1 bp of 500 differed) with *Enterococcus avium*. Greater than 97% homology was also observed with $E_1$ *gilvus* (99.84), *E. malodoratus* (98.63), *E. pseudoavium* (98.21), and *E. Raffinosus* (97.89). Generally, greater than 97% homology is commonly used as a benchmark for species identity of bacteria.

Having described the present invention, it will be apparent that changes and modifications may be made to the above-described embodiments without departing from the sprit and the scope of the present invention.

All volume or percentage of figures stated in the application are stated as volume/volume, unless stated otherwise or clearly contradicted by the context.

All references, including publications, patent applications, patents, and website content cited herein are hereby incorporated by reference to the same extent as if each reference were individually and specifically indicated to be incorporated by reference and was set forth in its entirety herein.

The use of the terms "a" and "an" and "the" and similar referents in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A method for producing butanol from anaerobic microbial fermentation of a gaseous substrate, the method comprising:
   a) culturing microorganisms in a fermentation broth in a reactor vessel and supplying to said reactor vessel said gaseous substrate comprising at least one gas selected from hydrogen, carbon monoxide, and carbon dioxide;
   b) manipulating partial pressure of each of said at least one gas selected from hydrogen, carbon monoxide, and carbon dioxide in the reactor vessel so that it is thermodynamically feasible to convert said gaseous substrate to butanol;
   c) said culturing and manipulating steps causing said microorganisms in said reactor vessel to produce the butanol in the fermentation broth, wherein said fermentation broth comprises at least 0.5% butanol by volume.

2. The method of claim 1, wherein the reactor vessel also contains cellulosic biomass which is also converted to butanol.

3. The method of claim 1, wherein volume of butanol is at least 1% of volume of the fermentation broth, and said butanol is separated from the fermentation broth.

4. The method of claim 1, wherein the fermentation broth is maintained at a temperature greater than 30° C.

5. The method of claim 1, wherein total gas pressure is greater than one atmosphere.

6. The method of claim 1, wherein total gas pressure is greater than 2 atmospheres.

7. The method of claim 1, wherein the partial pressure of hydrogen is greater than 1 atmosphere.

8. The method of claim 1, wherein hydrogen is provided from electrolysis or a chemical reducing agent.

9. The method of claim 1, wherein carbon dioxide is provided by fermentation of biomass.

10. The method of claim 1, wherein conversion of said gaseous substrate to butanol enables said microorganisms to capture Gibbs free energy for maintenance or growth.

11. A method to isolate an alcohol-tolerant microorganism that converts hydrogen gas and at least one gas from carbon dioxide and carbon monoxide to butanol, the method comprising:
   a) growing a culture of microorganisms in a fermentation broth comprising at least 0.5% butanol by volume;
   b) growing said culture of microorganisms in a fermentation broth within a reactor vessel with hydrogen gas and at least one gas from carbon dioxide and carbon monoxide under reaction conditions that make it thermodynamically feasible to convert the hydrogen and at least one gas from carbon dioxide and carbon monoxide to said butanol, and
   c) isolating a microorganism that produces said butanol from said culture.

12. The method of claim 11, wherein the broth contains at least 1% butanol by volume.

13. The method of claim 11, wherein the reaction conditions include a total pressure in the reactor vessel of more than 1 atmosphere.

14. The method of claim 11, wherein the reaction conditions favor production of butanol over production of ethanol and over production of butyrate.

15. An isolated microorganism obtained by the method of claim 11, wherein said microorganism comprises genes that encode enzymes enabling uptake and conversion of carbon monoxide, or carbon dioxide to butanol, and wherein said isolated microorganism grows in a fermentation broth comprising at least 0.5% butanol by volume.

16. The isolated microorganism of claim 15, wherein said isolated microorganism produces butanol from at least one of hydrogen, carbon monoxide, or carbon dioxide.

17. The isolated microorganism of claim 15, wherein said isolated microorganism was selected for its ability to grow in a fermentation broth containing at least 1% butanol by volume of the fermentation broth.

18. The isolated microorganism of claim 15, wherein said microorganism grows in a fermentation broth with at least 3% butanol by volume.

19. The isolated microorganism of claim 15, wherein said microorganism is aerotolerant.

20. The isolated microorganism of claim 15, having a 16S rRNA sequence, which is at least 97% identical with that for Enterococcus avium.

* * * * *